United States Patent
Meissner et al.

(10) Patent No.: US 12,203,916 B2
(45) Date of Patent: Jan. 21, 2025

(54) SYSTEMS AND METHODS FOR SOIL ANALYSIS INCLUDING PENETROMETER WITH SPIRAL FLIGHTING

(71) Applicant: Yard Stick PBC, Dover, DE (US)

(72) Inventors: Kevin Andrew Meissner, Oakland, CA (US); Christopher Mencke Tolles, Cambridge, MA (US)

(73) Assignee: Yard Stick PBC, Dover, DE (US)

( * ) Notice: Subject to any disclaimer, the term of this patent is extended or adjusted under 35 U.S.C. 154(b) by 180 days.

(21) Appl. No.: 17/977,946

(22) Filed: Oct. 31, 2022

(65) Prior Publication Data

US 2023/0132655 A1  May 4, 2023

Related U.S. Application Data

(60) Provisional application No. 63/274,453, filed on Nov. 1, 2021.

(51) Int. Cl.
| | |
|---|---|
| *G01N 33/24* | (2006.01) |
| *G01N 9/00* | (2006.01) |
| *G01N 21/31* | (2006.01) |

(52) U.S. Cl.
CPC .............. *G01N 33/24* (2013.01); *G01N 9/00* (2013.01); *G01N 21/31* (2013.01); *G01N 2201/08* (2013.01)

(58) Field of Classification Search
CPC .......... G01N 33/24; G01N 9/00; G01N 21/31; G01N 2201/08; G01N 21/3554;
(Continued)

(56) References Cited

U.S. PATENT DOCUMENTS

| | | | |
|---|---|---|---|
| 6,317,694 B1 | 11/2001 | Kram et al. | |
| 7,234,362 B2 | 6/2007 | Shinn, II et al. | |

(Continued)

FOREIGN PATENT DOCUMENTS

| | | |
|---|---|---|
| CN | 110470614 A | 11/2019 |
| WO | WO 2005/003728 A2 | 1/2005 |

OTHER PUBLICATIONS

Poggio, Matteo, David J. Brown, and Ross S. Bricklemyer. "Laboratory-based evaluation of optical performance for a new soil penetrometer visible and near-infrared (VisNIR) foreoptic." Computers and Electronics in Agriculture 115 (2015): 12-20. (Year: 2015).*

Poggio et al., Laboratory-based evaluation of optical performance for a new soil penetrometer visible and near-infrared (VisNIR) foreoptic. Computers and Electronics in Agriculture. Jul. 2015;115:12-20.

(Continued)

*Primary Examiner* — Eric S. McCall
*Assistant Examiner* — Timothy P Graves
(74) *Attorney, Agent, or Firm* — Wolf, Greenfield & Sacks, P.C.

(57) ABSTRACT

Systems and methods for analyzing soil are generally provided. In particular, the disclosure provides systems and methods for determining bulk density of soil using rotational soil penetrometers. In some embodiments, the bulk density is determined by obtaining spectroscopic data and penetration torque data from the rotational soil penetrometer, and determining the bulk density of the soil based at least in part on the spectroscopic data and the penetration torque data. Bulk density may be combined with in situ measurements of elemental composition (e.g., carbon content) of soil in order to calculate total quantities of an element (e.g., carbon) in an area's topsoil. Also disclosed herein are systems and methods for modeling bulk density and/or carbon content of soil, based at least in part on spectroscopic data and penetration (Continued)

torque data. For example, trained statistical models determination are provided herein.

24 Claims, 21 Drawing Sheets

(58) Field of Classification Search
CPC .............. G01N 21/255; G01N 33/245; G01N 21/3563; G01N 2021/855; G01N 2201/1296; G01N 33/246
See application file for complete search history.

(56) References Cited

U.S. PATENT DOCUMENTS

| | | |
|---|---|---|
| 10,337,159 B2 | 7/2019 | Morgan et al. |
| 10,845,353 B2 | 11/2020 | Viscarra Rossel et al. |
| 2006/0158652 A1 | 7/2006 | Rooney et al. |
| 2011/0106451 A1 | 5/2011 | Christy et al. |
| 2017/0370064 A1 | 12/2017 | Morgan et al. |
| 2019/0285608 A1 | 9/2019 | Laird et al. |
| 2020/0128723 A1 | 4/2020 | Eichhorn |

OTHER PUBLICATIONS

International Search Report and Written Opinion mailed Mar. 27, 2023 in connection with International Application No. PCT/US22/48447.

Cambou et al., Prediction of soil organic carbon stock using visible and near infrared reflectance spectroscopy (VNIRS) in the field. Geoderma, Elsevier, Nov. 2015. vol. 261, V2, 21 pages. (10.1016/geoderma.2015.07.007). (ird-01224957).

Murad et al., In-Situ Estimation of Soil Organic Carbon Concentrations and Stocks Along the Soil Profile Using a Penetrometer. ASA, CSSA, SSSA International Annual Meeting. Nov. 9, 2021. in Salt Lake City, UT. https://scisoc.confex.com/scisoc/2021am/meetingapp.cgi/Paper/138769.

* cited by examiner

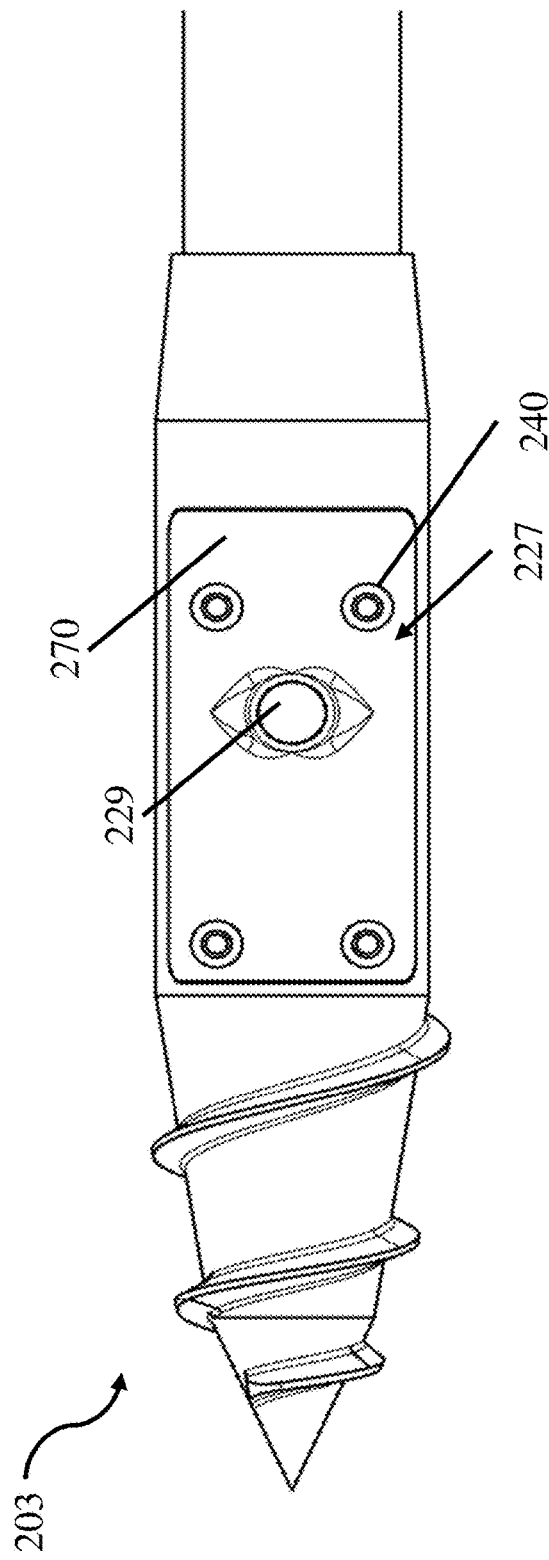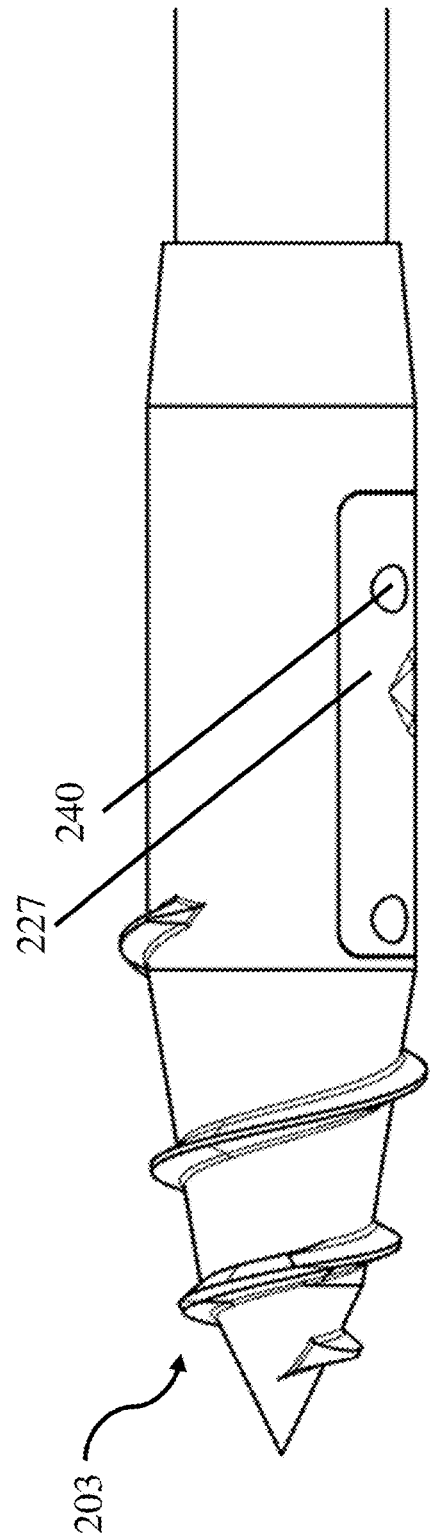
FIG. 2A
FIG. 2B

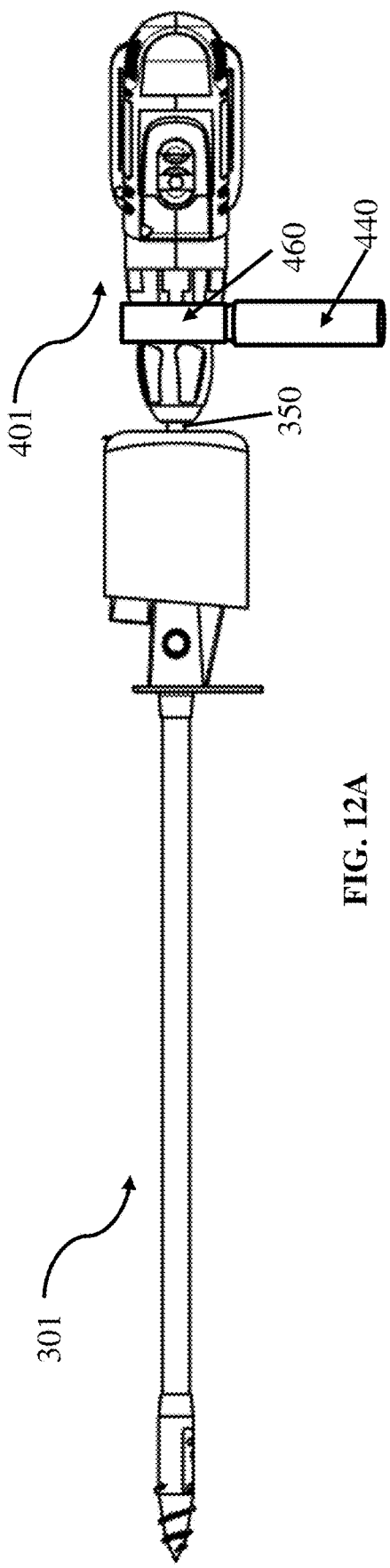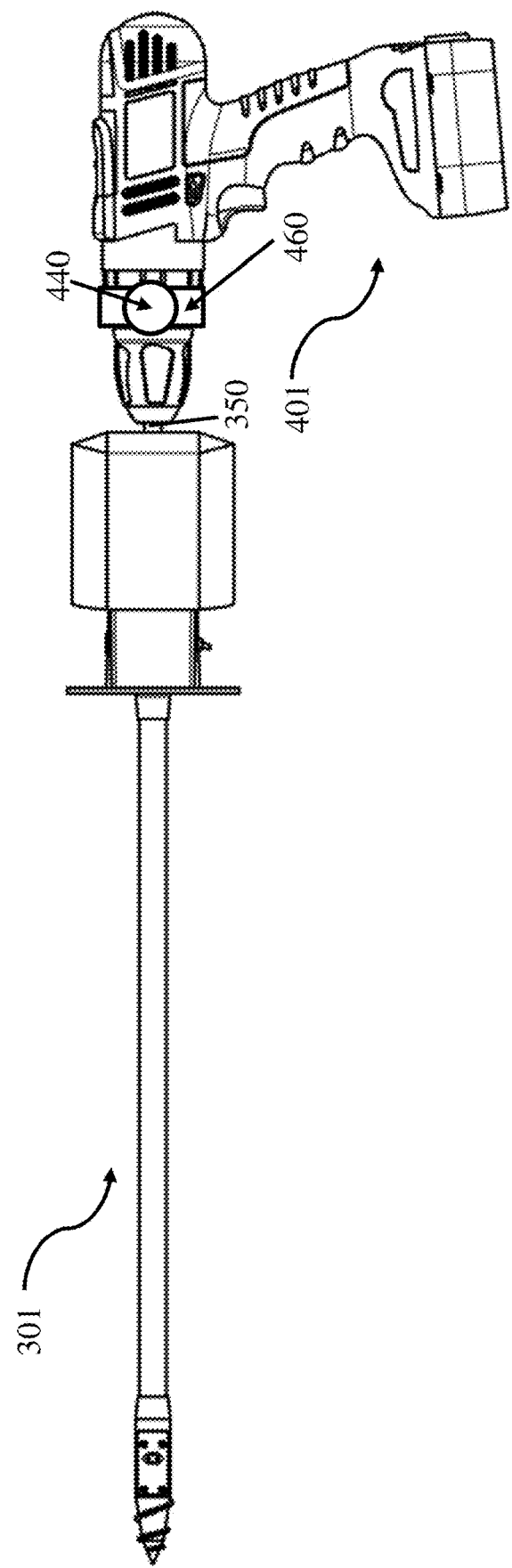
FIG. 12A
FIG. 12B

SYSTEMS AND METHODS FOR SOIL ANALYSIS INCLUDING PENETROMETER WITH SPIRAL FLIGHTING

CROSS-REFERENCE TO RELATED APPLICATIONS

This application claims the benefit under 35 U.S.C. § 119(e) of U.S. provisional application Ser. No. 63/274,453, filed Nov. 1, 2021, the disclosures of which are incorporated by reference in their entirety.

GOVERNMENT SPONSORSHIP

This invention was made with Government support under Contract No. DE-AR0001384 awarded by the U.S. Department of Energy. The Government has certain rights in the invention.

FIELD

Disclosed embodiments are related to systems and methods for soil analysis.

BACKGROUND

Linear soil penetrometers have been used to spectroscopically identify the relative abundance of elemental constituents of soil, such as carbon. These results may be combined with bulk density measurements of soil, collected from separate soil samples extracted for separate laboratory analysis, to determine the total mass of the elemental constituents of the soil.

SUMMARY

Systems and methods for analyzing soil are generally provided. In particular, the disclosure provides systems and methods for determining bulk density of soil using rotational soil penetrometers. In some embodiments, the bulk density is determined by obtaining spectroscopic data and penetration torque data from the rotational soil penetrometer, and determining the bulk density of the soil based at least in part on the spectroscopic data and the penetration torque data. Bulk density may be combined with in situ measurements of elemental composition (e.g., carbon content) of soil in order to calculate total quantities of an element (e.g., carbon) in an area's topsoil. Also disclosed herein are systems and methods for modeling bulk density and/or carbon content of soil, based at least in part on spectroscopic data and penetration torque data. For example, trained statistical models determination are provided herein.

In one aspect, a method for determining bulk density of a soil is provided. In some embodiments, the method for determining bulk density of a soil comprises: obtaining soil data that includes spectroscopic data collected from a rotational soil penetrometer and penetration torque data collected from the rotational soil penetrometer during collection of the spectroscopic data; and determining the bulk density of the soil based at least partly on the spectroscopic data and the penetration torque data.

In another aspect, a method for determining bulk density of a soil is provided. In some embodiments, the method for determining bulk density of a soil, the method comprises: obtaining soil data that includes spectroscopic data collected from a soil penetrometer and penetration torque data collected from the soil penetrometer during collection of the spectroscopic data; obtaining one or more geographic locations associated with the soil data; and determining the bulk density of the soil based at least partly on the spectroscopic data, the penetration torque data, and the one or more geographic locations.

In yet another aspect, at least one non-transitory computer-readable storage medium is provided. In some embodiments, the at least one non-transitory computer-readable storage medium stores programming instructions that, when executed by at least one processor, causes the at least one processor to perform a method for determining a bulk density of a soil, the method comprising: obtaining soil data that includes spectroscopic data collected from a rotational soil penetrometer and penetration torque data collected from the rotational soil penetrometer during collection of the spectroscopic data; and determining the bulk density of the soil, based at least in part on the spectroscopic data and the penetration torque data.

In still another aspect, at least one non-transitory computer-readable storage medium is provided. In some embodiments, the at least one non-transitory computer-readable storage medium stores programming instructions that, when executed by at least one processor, causes the at least one processor to perform a method for determining a bulk density of a soil, the method comprising: obtaining soil data that includes spectroscopic data collected from a soil penetrometer and penetration torque data collected from the soil penetrometer during collection of the spectroscopic data; obtaining one or more geographic locations associated with the soil data; and determining the bulk density of the soil, based at least in part on the spectroscopic data, the penetration torque data, and the one or more geographic locations.

In one aspect, a rotational soil penetrometer is provided. In some embodiments, the rotational soil penetrometer comprises: a spectrometer; a head comprising a spiral flighting extending along at least a portion of a length of a distal portion of the head; a shaft extending from a proximal end portion of the head; and a cavity formed in the head, wherein the cavity is configured to selectively receive an optics module, wherein the optics module is operatively coupled to the spectrometer through the shaft when the optics module is received in the cavity.

In another aspect, a rotational soil penetrometer is provided. In some embodiments, the rotational soil penetrometer, comprises: a head; a shaft extending from a proximal end portion of the head; a bracket, mechanically coupled to a proximal end portion of the shaft; a torque sensor, configured to measure penetration torque data associated with the rotation of the head into soil; and a spectrometer mechanically coupled to the shaft and optically coupled to a portion of the head.

In still another aspect, a method for determining bulk density of a soil is provided. In some embodiments, the method comprises: obtaining soil data that includes: spectroscopic data collected from the soil; and mechanical soil data; providing the soil data to a trained statistical model; and determining the bulk density of the soil using the trained statistical model.

In yet another aspect, a method of training a statistical model. According to some embodiments, the method comprises: obtaining soil bulk densities; obtaining soil training data, wherein the soil training data includes soil spectroscopic data and mechanical soil data; generating a trained statistical model using the soil bulk densities and training data; and storing the trained statistical model in non-transitory computer readable memory for subsequent use in determining soil bulk densities.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings:

FIG. 2A presents a side-view schematic illustration of an exemplary rotational soil penetrometer head comprising an optics module, according to some embodiments;

FIG. 2B presents a side-view schematic illustration of an exemplary rotational soil penetrometer head comprising an optics module, according to some embodiments;

FIG. 12A presents a top-view schematic illustration of an exemplary rotational soil penetrometer coupled to a drive system, according to some embodiments;

FIG. 12B presents a side-view schematic illustration of an exemplary rotational soil penetrometer coupled to a drive system, according to some embodiments;

DETAILED DESCRIPTION

Figure 1A:
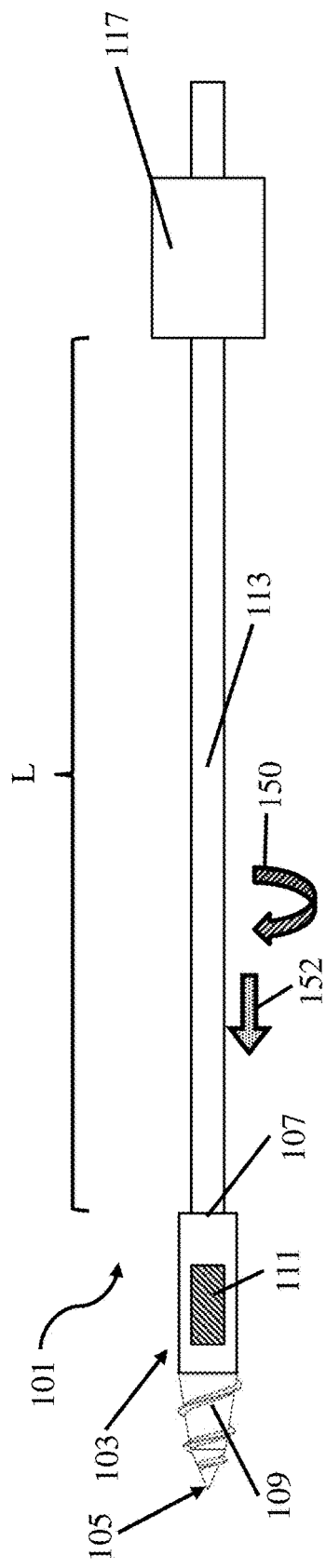
FIG. 1A presents a side-view schematic illustration of an exemplary rotational soil penetrometer, according to some embodiments.

Systems and methods for analyzing soil are generally provided. In particular, the disclosure provides systems and methods for determining bulk density of soil using rotational soil penetrometers. In some embodiments, the bulk density is determined by obtaining spectroscopic data and penetration torque data from the rotational soil penetrometer, and determining the bulk density of the soil based at least in part on the spectroscopic data and the penetration torque data, though other data may be optionally be used, as detailed further below. Bulk density may be combined with the determined one or more elemental compositions of the soil (e.g., carbon content), in order to calculate total quantities of an element (e.g., carbon) in an area's soil. Also disclosed herein are systems and methods for modeling bulk density of soil, based at least in part on spectroscopic data and penetration torque data.

Linear soil penetrometers have a number of disadvantages. For example, linear penetrometers may require a high penetration force to penetrate soil, and may require significant reinforcement against this penetration force. As a result, linear soil penetrometers are often heavy, requiring mounting on vehicles or frames. This can significantly reduce portability, and increase price. Furthermore, linear soil penetrometers may be difficult to transport, and may be limited to certain geographic areas or terrain types.

In view of the above, the Inventors have recognized that rotational soil penetrometers may provide several advantages over linear soil penetrometers for determining the bulk density of soil. For example, rotational soil penetrometers may advantageously allow measurement of penetration torque data. In the context of the present disclosure, it has been recognized that penetration torque data collected from soil, alongside spectroscopic data collected from the soil, can be used to identify the bulk density of the soil in situ. For example, bulk density of the soil may be calculated using a model based on rotational soil penetrometer measurements. By measuring bulk density in situ, rather than by coring and subsequently analyzing the soil in the laboratory, the systems and methods described herein may provide significant advantages for analyzing soil properties.

The Inventors have also recognized that the more portable and easily used systems and methods disclosed herein may permit the measurement and characterization of soil properties in different geographic locations. Thus, the Inventors have recognized another advantage of the rotational soil penetrometers described herein is that, in some embodiments, the rotational soil penetrometer may be configured to determine a geographic location of the penetrometer during use. Using this geographic location data, location specific calibration data may be used to analyze the measured data to provide both an accurate and easy to use system in any number of locations without the need for a user to conduct costly and time consuming calibration testing, in some embodiments, as detailed further below.

In the present disclosure, it has also been recognized that rotational soil penetrometers may provide several design advantages. For example, rotational soil penetrometers may be comparatively small, more portable, and inexpensive. Rotational penetrometers may also require a relatively low penetration force for soil insertion, and may consequently require relatively low structural reinforcement (and less weight). Advantageously, rotational penetrometers may remove the need for vehicle mounts or frames to support.

A rotational soil penetrometer may be used to obtain soil data, in some embodiments. According to certain embodiments, the rotational soil penetrometer may be rotated to position a distal end portion of the penetrometer, such as a head including one or more sensors, in soil. In some embodiments, the rotational soil penetrometer is configured to collect mechanical penetration data (e.g., penetration torque data and/or penetration force data). The rotational soil penetrometer may also be configured to collect spectroscopic data. In some embodiments, the rotational soil penetrometer is configured to determine the properties of soil. For example, the rotational soil penetrometer may be configured to determine bulk density of the soil, elemental composition of the soil (e.g. carbon content of the soil, nitrogen content of the soil, oxygen content of the soil), soil moisture, soil texture, and/or any of a variety of other soil properties based at least in part on the soil penetration data and/or the spectroscopic data.

A penetrometer provided herein may be particularly useful for the analysis (e.g., for the determination of carbon content) of soil. Spectrographic signals of soil are, in some embodiments, complex and non-linear. Conventional methods have relied on air-drying of soil and establishment of at least some properties, prior to spectrographic analysis. Such methods may simplify analysis—but they make it difficult to reliably measure soil in situ, and therefore prior systems have been unable to accurately capture local variations in soil properties that occur in the ground.

In contrast, the present disclosure is directed, according to some embodiments, towards modeling techniques suitable for addressing the complexity and non-linearity of spectrographic analysis of soil in situ. The penetrometers herein may help to overcome the problems of conventional laboratory analysis by permitting rapid acquisition of high quality training data, collected from heterogeneous, locally variable soil environments. In particular, these methods may be advantageous for the analysis of wet soil, where conventional benchtop analysis has failed to provide reliable methods of determining soil properties such as carbon content. In contrast, using a penetrometer provided herein, the properties of wet soil may be established directly, e.g., by the use of an appropriate model described elsewhere herein. This may, advantageously, permit in situ measurements of the soil, according to some embodiments. However, it should be understood that the disclosed models may be used to determine soil properties using in situ measurements, pre-collected soil samples, bench top measurements, and/or any appropriate measurements obtained using any appropriate measurement system including sensors other than those disclosed herein as the disclosure is not so limited. The disclosed models may also be calibrated to work on only dry soil samples, only wet soil samples, or both wet and dry soil samples depending on the desired application.

Using the systems and methods described herein, the bulk density of the soil may be determined using soil data, in some embodiments. For example, the bulk density of the soil may be determined based, at least in part, on spectroscopic data and the mechanical soil data, such as penetration torque data, in some embodiments. Optionally, the bulk density of the soil may be determined based, at least in part, on mechanical soil data such as penetration force data. Of course other types of mechanical soil data may also be used to characterize the mechanical properties of the soil. Additionally, other data (e.g., geographic location) may also be incorporated into the determination of bulk density of the soil in some embodiments.

In some embodiments, a rotational soil penetrometer may be used to collect mechanical soil data. The rotational soil penetrometer may be used to collect penetration torque data (e.g., torque associated with rotation of the rotational soil penetrometer into soil). The rotational soil penetrometer may also be configured to collect penetration force data (i.e., data on linear penetration force that does not produce a rotational torque around a longitudinal axis of a shaft of the rotational soil penetrometer). As described above, mechanical soil data such as penetration torque data and/or penetration force data may be used to aid in determining bulk density of the soil. However, spectroscopic soil data may also be used to determine other properties of the soil for aiding in determining the bulk density of the soil. For example, spectroscopic soil data may be used to determine, or may be representative of, soil texture and/or soil moisture, in some embodiments. In some embodiments, mechanical soil data are collected concurrently with spectroscopic data, such that the mechanical soil data (e.g., penetration torque, penetration force, and/or other data) are collected during collection of spectroscopic data. The mechanical soil data and spectroscopic data may be coordinated with one another such that each mechanical soil data point, or set of points, is associated with a corresponding spectroscopic data point, or set of points, at a given collection time point or period of time in some embodiments. Additionally, while the embodiments described herein are primarily directed to using rotational based soil penetrometers, in some embodiments, the various analysis methods, including the use of trained statistical models may be implemented using other types of spectrometers including soil penetrometers, contact spectrometers, bench top spectrometers, and/or any other appropriate type of system that may be used to perform reflectance spectroscopy on a soil sample of any size, shape, and/or form (i.e., a bore the probe is inserted into, a soil core, loose soil samples, etc.).

According to certain embodiments, a rotational soil penetrometer, or other soil measurement system and/or technique, may be used at one or more geographic locations. Different soils in different geographic locations often have different properties (e.g., different mineral compositions, different textures). For example, soil may have different contents of sand, clay, peat, silt, chalk, and/or loam, depending on the geographic location. As a result, a trained model may be calibrated for a particular geographic region. Calibrations and/or calibrated models suitable to one geographic location may not be suitable for another. Thus, different geographic locations may require different models and/or calibrations. Linear soil penetrometers, as a result of their size, weight, and mode of use, are relatively expensive and/or nonportable, reducing their ability to map and model soil data associated with multiple locations. In contrast, rotational soil penetrometers may be comparatively portable. In some embodiments, rotational soil penetrometers described herein may determine a position of the penetrometer during use such that the measured data may be analyzed with one or more calibrated models selected from separate calibrated models associated with different geographic locations. Advantageously, this may allow the use of the rotational soil penetrometers anywhere in the world. However, it should be understood that such an implementation may also be used with linear penetrometers and/or other soil sampling techniques as well as the current disclosure is not limited to using geographic information only with rotational penetrometers.

In view of the above, in some embodiments, a method comprises obtaining one or more geographic locations associated with soil data. Bulk density of the soil may be determined at least partially based on the one or more geographic locations. For example, based on a geographic location, an appropriate model and/or calibration for a model of bulk density of the soil made be identified, and soil data from the soil penetrometer may be provided to the calibrated model associated with the geographic location of the measurements in order to determine the bulk density of the soil. Having calibrated models for different geographic locations that may be selected from based on a geographic location of the measured data may improve the global accuracy of the disclosed systems.

In one aspect, a database is provided. The database may include training data associated with a plurality of geographic locations. In some embodiments, the database may be provided with training data from a first geographic region. For example, the database may be provided with training data from a rotational soil penetrometer at a geographic location within the first geographic region. The training data may be used to train a statistical model, which may correspond to a calibrated model in some embodiments, as elaborated on further below. This process may be repeated for multiple geographic locations. In some embodiments, the database may associate a geographic region with the resulting trained statistical models. In some embodiments, a penetrometer may transmit soil data and a geographic location to a remotely located computing device associated with the database to implement the methods disclosed herein. Alternatively, the database may be configured to transmit a trained statistical model and/or calibration data for the statistical model to a system for use. The database may transmit the trained statistical model and/or the calibration data for the statistical model in response to the provided data including the first geographic location. Alternatively, a plurality of calibrated models associated with different geographic locations may already be loaded on a system prior to use as the disclosure is not so limited. Accordingly, it should be understood that models implementing information related to a geographic location of measured data may be implemented in any number of ways.

As explained above, in some embodiments, a rotational soil penetrometer may be used to collect spectroscopic data. The spectroscopic data may be collected using any of a variety of appropriate techniques. For example, spectroscopic data may be collected using reflectance spectroscopy. In some embodiments, the spectroscopic data includes reflectance data from illuminated soil (e.g., from soil that has been illuminated by a rotational soil penetrometer). The spectroscopic data may be collected using a spectrometer. The spectrometer may be part of a rotational soil penetrometer, as described in greater detail below, with reference to the figures. The spectroscopic data may, in some cases, be used to measure soil properties. In some embodiments, the spectroscopic data may be used to determine the elemental composition of the soil. For example, in some embodiments, the spectroscopic data may be used to determine carbon content, nitrogen content, oxygen content, clay content, cation exchange capacity, soil texture, and/or moisture (water content) of soil. In some embodiments, the content of other species and/or elements in the soil may be determined spectroscopically, and the disclosure is not so limited. The above soil parameters may be determined from the spectroscopic data using an appropriately trained model as detailed further herein. The content of a species in soil may be quantified as a weight percentage (wt. %) of the soil. Thus, an advantage of simultaneously determining the bulk density of soil in a given position is the ability to determine a volumetric mass density of the species, by multiplying the weight percentage of the species by the density of species. For example, if the density of soil is determined to be 2 $g/cm^3$, and the soil is 20% carbon, the volumetric density of carbon is 0.4 $g/cm^3$. This may, advantageously, allow calculation of a total amount of carbon in the soil by multiplying the soils volume by its average carbon density. Similar calculations may be performed for other species identifiable in the soil.

The spectroscopic measurements described herein may be performed using any appropriate wavelength or band of wavelengths depending on the specific application. However, in some embodiments, the spectroscopic measurements may be conducted using ultraviolet (UV) spectroscopy (i.e., spectroscopy at wavelengths between 100 nm and 380 nm); visible light (VIS) spectroscopy (i.e., spectroscopy at wavelengths between 380 nm and 750 nm); infrared (IR) spectroscopy (i.e., spectroscopy at wavelengths between 750 nm and 1000000 nm) including near-IR (NIR) (wavelengths between 750 nm and 2500 nm) or mid-IR spectroscopy (wavelengths between 2500 and 25000 nm); as well as combinations of the above (e.g., UV-VIS spectroscopy or UV-VIS-IR spectroscopy).

In some embodiments, IR spectroscopy may be advantageous for analyzing an elemental content and other properties of soil. In some embodiments, spectroscopic data may be collected at wavelengths greater than or equal to 750 nm, greater than or equal to 1000 nm, greater than or equal to 1200 nm, greater than or equal to 1500 nm, greater than or equal to 1800 nm, greater than or equal to 2000 nm, greater than or equal to 2500 nm, or greater. In some embodiments, the spectroscopic data may be collected at wavelengths less than or equal to 5000 nm, greater than or equal to 4000 nm, greater than or equal to 3000 nm, less than or equal to 2800 nm, less than or equal to 2500 nm, less than or equal to 2200 nm, less than or equal to 2000 nm, less than or equal to 1500 nm, or less. Combinations of these ranges are possible. For example, in some embodiments, the spectroscopic data may be collected at wavelengths greater than or equal to 750 nm and less than or equal to 5000 nm. As another example, in some embodiments, the spectroscopic data may be collected at wavelengths greater than or equal to 1000 nm and less than or equal to 3000 nm.

In some embodiments, the soil data comprises location data. For example, soil data may comprise geographic location data, in some embodiments. In some embodiments, location data comprises depth data. The location data soil may be collected using any appropriate method. At least some of the location data may be collected using a global navigation satellite system (GNSS). For example, at least some of the location data may be collected using a global positioning system (GPS). In some embodiments, a rotational soil penetrometer as described herein comprises a GNSS antenna, as described in greater detail below. According to some embodiments, the rotational soil penetrometer is connected to an external computing device (e.g., a phone, a computer) proximate to the rotational soil penetrometer that comprises a GNSS antenna. In other embodiments, the location data may comprise a manually entered location (e.g., a latitude, and/or a longitude associated with the rotational soil penetrometer, location data measured using cellular network localization, and/or any other appropriate method or system that may be used to determine a location associated with one or more sets of soil data.

In some embodiments, the location data may also include depth data. In some embodiments, depth data may be collected by the rotational soil penetrometer as it is penetrated into the soil. For example, as described in greater detail below, the rotational soil penetrometer may comprise a depth sensor. In some embodiments, the soil data may be recorded at multiple depths. It may be advantageous, in some embodiments, to record and/or correlate soil data at multiple depths, in order to characterize variation of a soil property at various depths. For example, by measuring depth alongside soil data, depth profiles of soil properties (e.g., texture, soil moisture, elemental composition of the soil, and/or bulk density of the soil may be produced).

A model is used to determine a soil property, in some embodiments. For example, in some embodiments, a model is used to determine bulk density of soil. As inputs, the model may take measured soil data (e.g. spectroscopic data and mechanical soil data), along with optional separately determined soil properties (e.g., moisture, texture, carbon content, and/or nitrogen content). The measured soil data may correspond to measurements made using the penetrometers disclosed herein, or other appropriate sensors. The soil properties may be determined separately using other types of sensors and/or laboratory techniques. Taken together, the soil data and/or soil properties may be used as training data to train a statistical model for subsequent use in determining one or more soil properties. Depending on the embodiment, the model may be trained to measure properties associated with dry and/or wet soil samples. The model may also be trained with training data from a specific geographic location in some embodiments to provide a location specific model in some embodiments as elaborated on below. It should be understood that an appropriately sized training data set may be used to train the statistical model. However, the current disclosure is not limited to any particular number of training data points. In some embodiments, the statistical model is a linear model (i.e., the soil property determined by the model has, to a good approximation, a linear dependence on measured variables). The model may be a nonlinear statistical model. In some embodiments, the model is a machine learning model (e.g., a neural network). In some embodiments, the model is a regression model (e.g., a linear regression model). In view of the above, it should be understood that any of a variety of suitable models may be used, and in general, the choice of model may depend on features of the soil data, such as the location where the soil was collected.

As noted above, the model may be a trained statistical model. The model may be trained to determine a soil property (e.g., bulk density of the soil) using training data comprising soil data associated with known values of the soil property. For example, the training data may comprise soil data collected by using a rotational soil penetrometer to analyze soil. Training data may comprise mechanical soil data, such as penetration torque data and/or penetration force data. In some embodiments, the training data comprises spectroscopic data as described above. The training data may comprise properties computed from spectroscopic data, such as soil moisture, clay content, soil texture, and/or elemental composition data (e.g., carbon content, nitrogen content, oxygen content). In addition to the measured mechanical data and spectroscopic data, as noted above, the training data may further comprise the actual measured values of the soil property to be modeled (e.g., bulk density of the soil though in some instances intermediate soil parameters such as soil texture, moisture content, etc. may also be determined using a separate model), corresponding to the soil data collected by the rotational soil penetrometer or other system, where the true values are determined by laboratory analysis or other appropriate method, according to certain embodiments. The trained statistical model may be configured to output a determination of a soil property. For instance, the trained statistical model may be configured to determine bulk density of soil in some embodiments.

Training data may be associated with (e.g., collected from) either one or a plurality of geographic locations. In some embodiments, the training data may be used to train a single model. However, the training data may, in some embodiments, be used to train multiple statistical models that are associated with the different geographic regions. Thus, different models may be associated with different geographic regions. For example, in some embodiments, the bulk density of soil in a first geographic region may be determined using a first model (e.g., a linear regression model) associated with the first geographic region, and the bulk density of soil in a second geographic region may be determined using a second model (e.g., a neural net) associated with the second geographic region. In some embodiments, the same model may be associated with different geographic regions, and may have different calibrations associated with each region. For example, in some embodiments, the bulk density of soil in a first geographic region is determined using a first model calibrated to the first geographic region, and the bulk density of soil in a second geographic region is determined using the first model calibrated to the second geographic region.

According to certain embodiments, a trained statistical model may be stored. For example, the trained statistical model may be stored on at least one non-transitory computer readable storage medium. Storing the trained statistical model may comprise storing weights and/or programming instructions associated with the trained statistical model on the non-transitory computer readable storage medium. The weights may be associated with the particular model. For instance, the weights may be weights associated with the various nodes of a neural net. The at least one non-transitory computer readable storage medium may be operatively linked to a processor and the storage medium may include processor executable instructions that when executed by the processor perform any of the methods disclosed herein. For example, in some embodiments, programming instructions and/or weights stored on the at least one non-transitory computer readable storage medium are executed by the processor to determine a soil property (e.g., bulk density of the soil) in response to soil data provided to the processor.

Turning to the figures, specific non-limiting embodiments are described in further detail. It should be understood that the various systems, components, features, and methods described relative to these embodiments may be used either individually and/or in any desired combination as the disclosure is not limited to only the specific embodiments described herein.

A rotational soil penetrometer may comprise a head and a shaft. FIG. 1A presents a side view schematic illustration of an exemplary rotational soil penetrometer 101, according to some embodiments. Rotational soil penetrometer 101 comprises a head 103 and a shaft 113 that extends in a proximal direction from a proximal end portion 107 of head 103. The head may be configured to penetrate soil. In some embodiments, the rotational soil penetrometer is configured such that the distal end of the head can be rotationally inserted into the soil. For example, referring again to FIG. 1A, the rotational soil penetrometer is configured such that a distal end 105 can be inserted into the soil. In some embodiments, the head narrows towards the distal end of the head (e.g., to a conical point). For example, referring again to FIG. 1A, head 103 narrows to a conical tip at distal end 105. The head may widen from the distal end towards the proximal end portion, in some embodiments. However, in some embodiments, the head has a relatively uniform diameter near the proximal end portion of the head. For example, as shown in FIG. 1A, in some embodiments, head 103 expands from the tip to a relatively uniform diameter extending along a proximal portion 107 of the head. The relatively uniform diameter may be useful in some embodiments in which spectroscopic data, or other data, is measured in a direction oriented radially outwards from this proximal portion of the head. For example, the relatively uniform diameter may, advantageously, help to ensure intimate contact between the soil and one or more measurement portions of the device, such as windows of an optics module disposed on a side surface of the head, as described below.

In some embodiments, the head comprises one or more spiral flightings extending along at least a portion of the head. For example, as shown in FIG. 1A, head 103 of rotational soil penetrometer 101 comprises a spiral flighting 109. The spiral flighting may extend along at least a portion of a length of the head from a distal location proximate to the tip 105 to a proximal location which may be adjacent to a distal end of the proximal portion 107 of the head. The proximal portion of the head may be free of the flighting in some embodiments. The spiral flighting may be configured to propel the rotational soil penetrometer through the soil during the rotation of the rotational soil penetrometer. For example, in some embodiments, rotation of the rotational soil penetrometer in a first rotational direction propels the rotational soil penetrometer in a first linear direction through the soil. In some embodiments, rotation of the rotational soil penetrometer in a second rotational direction opposite the first propels the rotational soil penetrometer in a second linear direction opposite the first through the soil. For example, referring again to FIG. 1A, spiral flighting 109 may be configured such that axial rotation of the rotational soil penetrometer in a first rotational direction 150 propels rotational soil penetrometer 101 in a first linear direction 152 into soil the head is positioned against. Rotation of rotational soil penetrometer 101 in a second rotational direction opposing first rotational direction 150 would propel rotational soil penetrometer 101 in a second linear direction out of the soil. In some embodiments, the rotational soil penetrometer experiences a penetration force opposing the direction of linear motion of the rotational soil penetrometer. For example, in FIG. 1A, the rotational soil penetrometer may experience a penetration force opposing the first linear direction of motion 152. The rotational soil penetrometer may further experience a penetration torque opposing a direction of rotational motion of the rotational soil penetrometer. For example, referring again to FIG. 1A, rotational soil penetrometer 101 may experience a penetration torque opposing the rotation of the rotational soil penetrometer in first rotational direction 150.

Figure 1B:
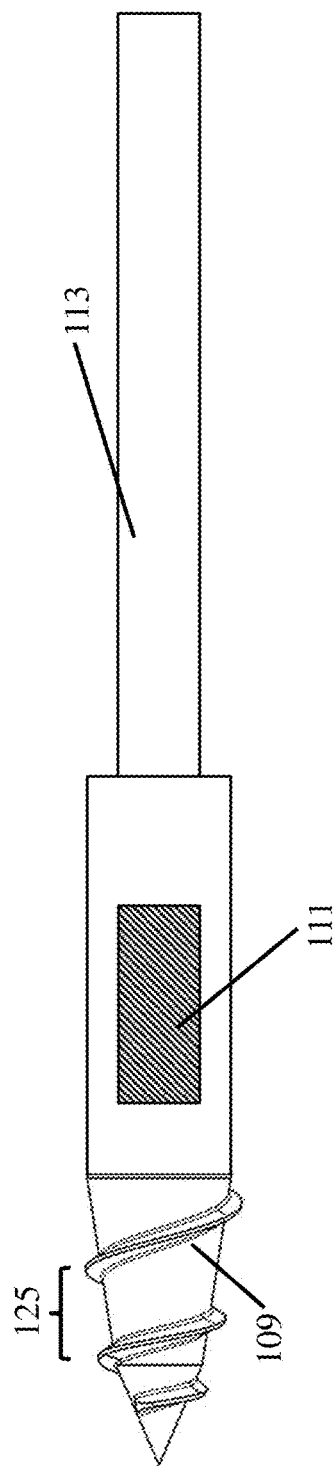
FIG. 1B presents a side-view schematic illustration of an exemplary rotational soil penetrometer head, according to some embodiments.

The spiral flighting may have a variable pitch. The pitch of the flighting may increase in a proximal direction along a length of the head. FIG. 1B presents a close up image of head 103 of rotational soil penetrometer 101 presented in FIG. 1A. As illustrated in the embodiments of FIG. 1B, a pitch 125 of spiral flighting 109 increases in the proximal direction along a length of the head. An increase in the pitch of the spiral flighting in the proximal direction along a length of the head may help to propel the rotational soil penetrometer through the soil by providing an increased volume between windings of the flighting to accommodate soil in areas of the head with larger areas.

The head, the shaft, and/or the spiral flighting may comprise any of a variety of appropriate materials. For example, the head, the shaft, and/or the spiral flighting may comprise an abrasion resistant material. In some embodiments the head, the shaft, and/or the spiral flighting comprise a metal such as steel, stainless steel. The metal may comprise hardening additives, in some embodiments. For example, the metal may comprise hardening additives such as tungsten carbide. According to some embodiments, the head, the shaft, and/or the spiral flighting comprise hardened steel, hardened titanium, or any other appropriate material offering a desired combination of strength and durability. In some embodiments, the head, the spiral flighting, and/or the shaft of the rotational soil penetrometer are coated. For example, the head, the shaft, or the spiral flighting of the rotational soil penetrometer may be coated in an abrasion resistant material. Of course, one of ordinary skill would understand that in the appropriate material for the head, the shaft, and/or the spiral flighting may be used, and that the disclosure is not limited to these materials.

As explained above, in some embodiments, the rotational soil penetrometer comprises a shaft extending from a proximal end portion of the head. For example, referring again to FIG. 1A, shaft 113 extends from proximal end portion 107 of head 103, in some embodiments. A diameter, or other maximum transverse dimension of the shaft may be narrower than a corresponding dimension of the head, such that the head broadens radially outwards from the shaft, in some embodiments. According to some embodiments, the narrowing of the shaft relative to the head may advantageously reduce penetration torque acting on the rotational soil penetrometer. Without wishing to be bound by theory, the penetration torque acting on the rotational soil penetrometer during rotation may increase with the width of the rotational soil penetrometer, as well as the depth of the rotational soil penetrometer in the soil. The increase in penetration torque with width may result from the increased surface area associated with greater width of the penetrometer, which may permit the application of more frictional force. The increase in penetration torque may also result from the fact that penetration torque resulting from frictional forces applied acting on the rotational soil penetrometer increases linearly with the distance between the frictional forces and the axis of rotation of the rotational soil penetrometer. In some embodiments, reducing penetration torque acting on the shaft of the rotational soil penetrometer, relative to the penetration torque acting on the head of the rotational soil penetrometer, may advantageously reduce the dependence of penetration torque on depth of the head.

Figure 1C:
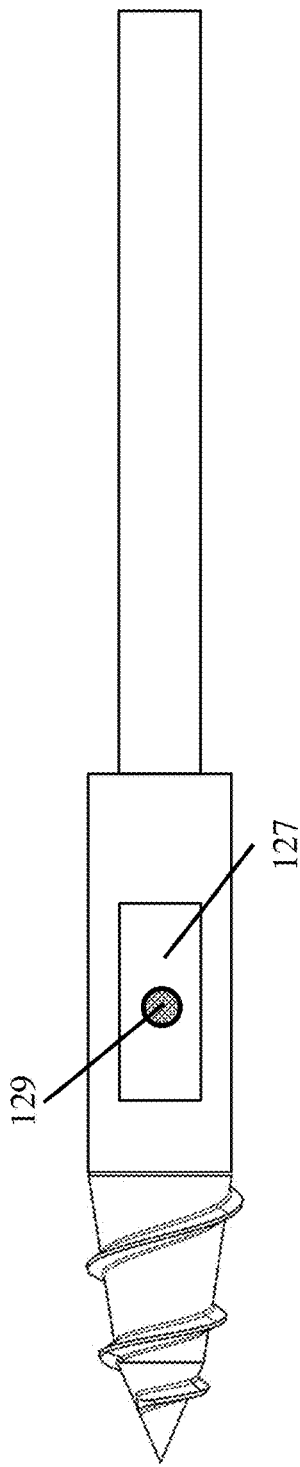
FIG. 1C presents a side-view schematic illustration of an exemplary rotational soil penetrometer head, according to some embodiments.

The shaft of the rotational soil penetrometer may have any appropriate length. The length of the rotational soil penetrometer may be measured from a proximal end portion of the head to a proximal end of the shaft extending out from a housing of the penetrometer (not depicted). For instance, rotational soil penetrometer 101 in FIG. 1 comprises shaft 113 having a length L. In some embodiments, the shaft has a length of greater than or equal to 5 cm, greater than or equal to 10 cm, greater than or equal to 20 cm, greater than or equal to 40 cm, greater than or equal to 60 cm, greater than or equal to 80 cm, or greater. In some embodiments, the shaft has a length of less than or equal to 120 cm less than or equal to 100 cm, less than or equal to 80 cm, less than or equal to 60 cm, less than or equal to 40 cm, or less. Combinations of these ranges are possible. For example, in some embodiments, the shaft has a length of greater than or equal to 5 cm and less than or equal to 120 cm. As another example, in some embodiments, the shaft has a length greater than or equal to 40 cm and less than or equal to 100 cm. Other lengths are also contemplated.

In some embodiments, the rotational soil penetrometer comprises a cavity. The cavity may be configured to receive an optics module. For example, the optics module may be at least partially removable from the cavity, such that the cavity can selectively receive the at least partially removed optics module. As an illustration, rotational soil penetrometer 101 of FIG. 1A comprises a cavity 111, which may be configured to receive an optics module 127. The cavity may comprise one or more optical components disposed therein. For example, the cavity may comprise a distal end of an optical fiber, as described in greater detail below. FIGS. 1A-1B illustrate rotational soil penetrometer 101, comprising cavity 111, according to some embodiments.

The disclosed penetrometers may be subjected to aggressive operating environments. Thus, in some embodiments, it may be desirable to replace the optics module in a system. Accordingly, the optics module may be at least partially removable and retained in the cavity as shown by the empty cavity and inserted optics module received therein as shown in FIGS. 1A-1B. For example, in FIG. 1C, the rotational soil penetrometer comprises an optics module 127 received in the cavity. While the embodiment of FIGS. 1A-1C comprises cavity 111 configured to receive optics module 127, it should of course be understood that the cavity and the at least partially removable optics module are optional features. For example, in some embodiments, the rotational soil penetrometer comprises a permanent optics module, as the disclosure is not so limited.

In some embodiments, the optics module is oriented radially outwards from the head. The optics module may comprise one or more optical components. For example, optics module 127 may comprise a window 129 that is oriented radially outwards on an outer surface of the head 103. The window may comprise a transparent material. For example, the window is configured to transmit light at a wavelength associated with a spectroscopic measurement of the rotational soil penetrometer, according to some embodiments. In some embodiments, the transparent material comprises a glass. For example, the transparent material may comprise an aluminosilicate glass, such as silica glass (quartz glass), alumina glass (sapphire glass), or any of a variety of other suitable aluminosilicate glasses or other glasses. In some embodiments, the window material is abrasion resistant. In some embodiments, the window may be degraded during rotation of the rotational soil penetrometer in soil. For example, the window is degraded by penetration torque and/or penetration force acting on the window. Thus, in some embodiments, the window is replaceable. For example, the entire optics module may be replaced with an optics module comprising a new window. In some embodiments, the optics module may be at least partially removed (e.g., the window may be removed) from the rotational soil penetrometer and replaced separately.

FIGS. 2A-2B present an exemplary head 203 comprising an optics module 227 in various orientations, according to some embodiments. As shown, optics module 227 may comprise a window 229. In some embodiments, such as the embodiment presented in FIGS. 2A-2B, window 229. Optics module 227 may be at least partially removed, as shown in FIGS. 2A-2B, by removing fasteners 240. Fasteners 240, as shown, may be configured to mechanically couple the optics module to the cavity. The fasteners may be screws, bolts, clips, pegs, and/or any of a variety of other appropriate types of fasteners suitable for mechanically coupling the optics module to the cavity. The fasteners may mechanically couple an external panel of the optics module to the cavity. For example, as shown in FIG. 2A, fasteners 240 mechanically couple external panel 270 to the cavity of penetrometer head 203. For example, cavity may comprise parts configured to interlock with the fasteners, holding them in position. For example, the cavity may comprise threaded cylinders, clips, holes, and/or any of a variety of suitable parts configured to interlock with the fasteners. The external panel may shield the optical components of the optics module from the soil. The external panel may comprise the window. For example, in FIG. 2A, external panel 270 comprises window 229. The external panel may be abrasion resistant.

Figure 3:
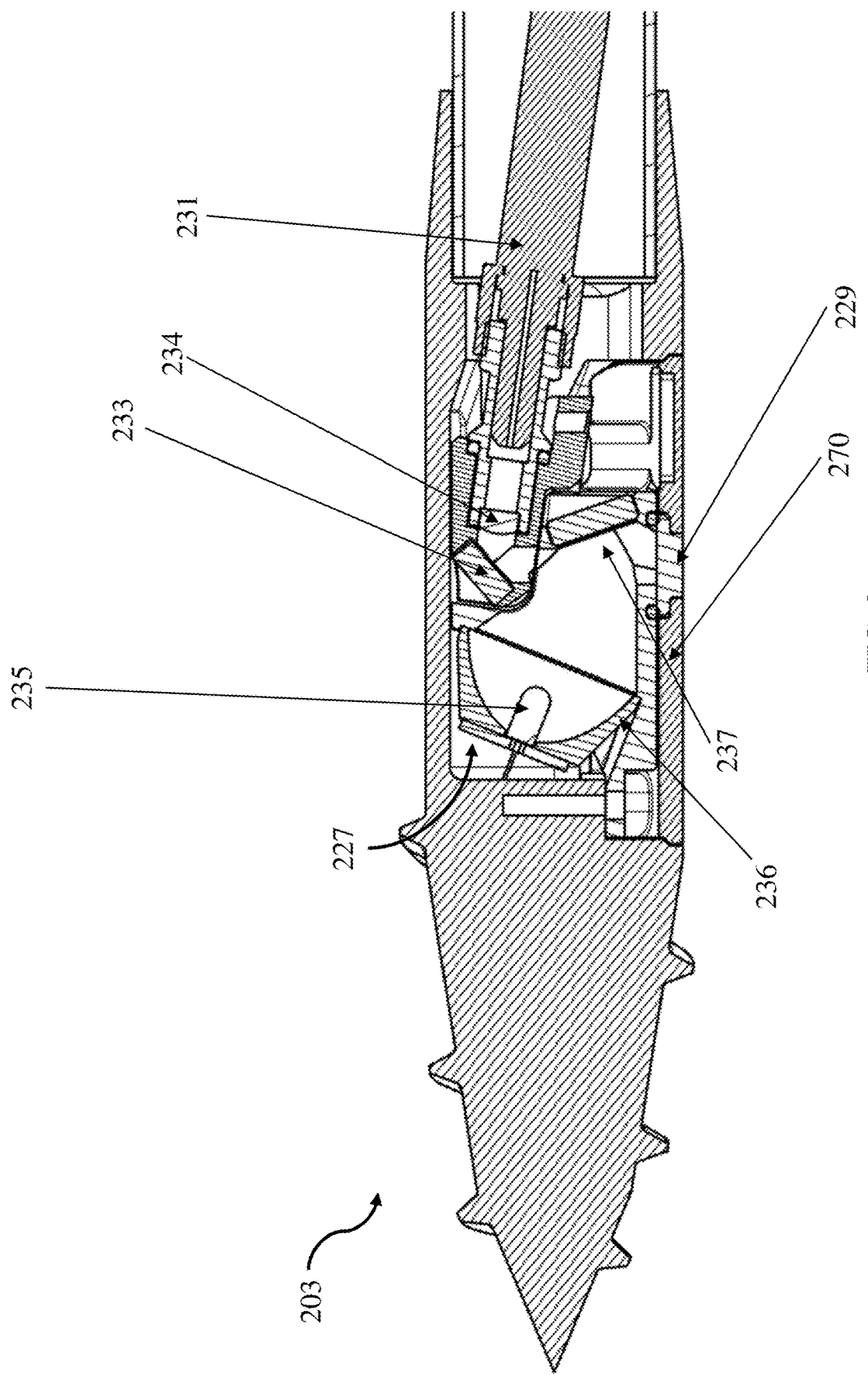
FIG. 3 presents a cross-sectional schematic illustration of an exemplary rotational soil penetrometer head comprising an optics module, according to some embodiments.

FIG. 3 provides a cross-sectional schematic illustration of head 203, illustrating components of the optics module 227 shown in FIGS. 2A-2B, according to some embodiments. According to certain embodiments, the optics module is optically connected to the spectrometer. For example, one or more optical fibers may transmit light collected by the optics module to the spectrometer. For instance, as shown in FIG. 3, optical fiber 231 may optically connect optics module 227 to a spectrometer (not shown). In some embodiments, the optics module is connected to a distal end portion of an optical fiber of the rotational soil penetrometer. For example, as shown in FIG. 3, in some embodiments, an optical fiber 231 is connected to optics module 227. The optical fiber may be configured to transmit light from the optics module to the spectrometer. For example, a proximal end portion of the optical fiber may be connected to the spectrometer, such that light from the distal end portion of the optical fiber is transmitted to the rotational soil penetrometer through the proximal end potion of the optical fiber. In some embodiments, the optics module is configured such that the optical fiber is optically coupled with one or more optical components of the optics module, as described in greater detail below. For example, as illustrated in FIG. 3, optical fiber 231 is optically coupled to collection optics 233 and 234, which are configured to direct light from the soil into the optical fiber. The collection optics may be of any appropriate type in configuration to direct the light reflected from the soil outside of the window to the one or more optical fibers. The specific arrangement shown in the figure is detailed further below.

As shown in FIG. 3, external panel 270 of optics module 227 comprises window 229 disposed therein and providing an optical path from an exterior of the head to the interior of the optics module, in some embodiments. In some embodiments, the external panel is flush with the fasteners and/or an external surface of the window, to help maintain a uniform distribution of frictional force acting on the penetrometer head by the soil. As another advantage, this may help maintain intimate contact between the soil and the external surface of the window, improving the measurement quality of the data. For example, in FIG. 3, the external surface of window 229 is flush with the external panel, since the window does not protrude from or recess into the surface 2 the external panel.

Window 229 may be optically coupled to and transmit light from a light source 235 situated within the optics module to soil adjacent to the window during operation. The light source may produce light at one or more wavelengths. In some embodiments, the light source produces light with a wavelength of greater than or equal to 50 nm, greater than or equal to 100 nm, greater than or equal to 200 nm, greater than or equal to 500 nm, greater than or equal to 1000 nm, greater than or equal to 1500 nm, greater than or equal to 2000 nm, or greater. In some embodiments, the light source produces light with a wavelength of less than or equal to 5000 nm, less than or equal to 3000 nm, less than or equal to 2000 nm, less than or equal to 1500 nm, less than or equal to 1000 nm, less than or equal to 500 nm, or less. Combinations of these ranges are possible. For example, in some embodiments, the light source produces light with a wavelength of greater than or equal to 50 nm and less than or equal to 5000 nm.

The optics module may comprise one or more illumination mirrors. For example, in FIG. 3, optics module 127 comprises illumination mirrors 236 and 237. An illumination mirror may be configured to concentrate the intensity of light. For example, in some embodiments, one or more illumination mirrors, or other optical components, are configured to direct light along a desired optical path to optically couple the light source with the window. FIG. 3 provides such an example, presenting an illumination mirror 236 adjacent to light source 235 that may be configured to focus light from light source 235. The illumination mirror may direct light onto a second illumination mirror 237. For example, as shown in FIG. 3, first illumination mirror 236 may be configured to redirect light emitted off axis from a desired optical path towards the second illumination mirror 237. However, embodiments in which this mirror is not included and a linear light source, such as a laser, is used are also contemplated. In either case, the emitted light may be directed towards the second illumination mirror 237 which redirects the light towards and through the window of the optics module. Thus, the light source may illuminate soil contacting a portion of the head 203 adjacent to the window. In some embodiments, the illumination mirrors are used to increase the relative intensity of light directed towards the soil. Increasing the intensity of light directed towards the soil may, advantageously, increase a spectroscopic signal arising from the soil. Thus, increasing the intensity of light directed towards the soil improves the accuracy of spectroscopic data, in some embodiments. However, other arrangements including configurations in which such a mirror is not used are also contemplated.

Any of a variety of light sources may be used in the rotational penetrometers described herein. For example, the light source may be an incandescent source (e.g., a tungsten-halogen light source), a gas discharge light source (e.g., a deuterium arc light source, a fluorescent light source, a xenon light source), a solid-state emission source (e.g., an LED light source, a laser light source), and/or a hybrid source. In some embodiments, the light source is a wavelength-tunable light source. In some embodiments, the light source is a fixed-wavelength light source.

In some embodiments, the optics module comprises collection optics. For example, optics module 227 comprises collection optics 233 and 234. The collection optics may comprise mirrors, prisms, lenses, and/or any other appropriate optical component configured to direct light reflected, or otherwise emitted, from the soil in response to the applied light from the light source 235 to a spectrometer (not depicted). For example, collection optics may comprise a mirror configured to reflect light emitted from the soil that passes through the window 229 into one or more optically coupled optic fibers 231. For example, as shown in FIG. 3, the optics module comprises mirror 233 that optically couples the optical fiber and the window. However, any of a variety of types of appropriate collection optics may be used, and one of ordinary skill in the art would be able to arrange the collection optics in a way that increased detection of light from the soil by the spectrometer.

In some embodiments, the optics module is configured such that light emitted from a light source 235 is directed towards a window 229 in the optics module. The window may transmit the light to soil intimately contacting an external surface of the window. Light reflected from the soil may then be directed into one or more optical fibers 231 or other optical component coupling the optics module with an associated spectrometer. Thus, an optical signal may be transmitted to the spectrometer.

Figure 4A:
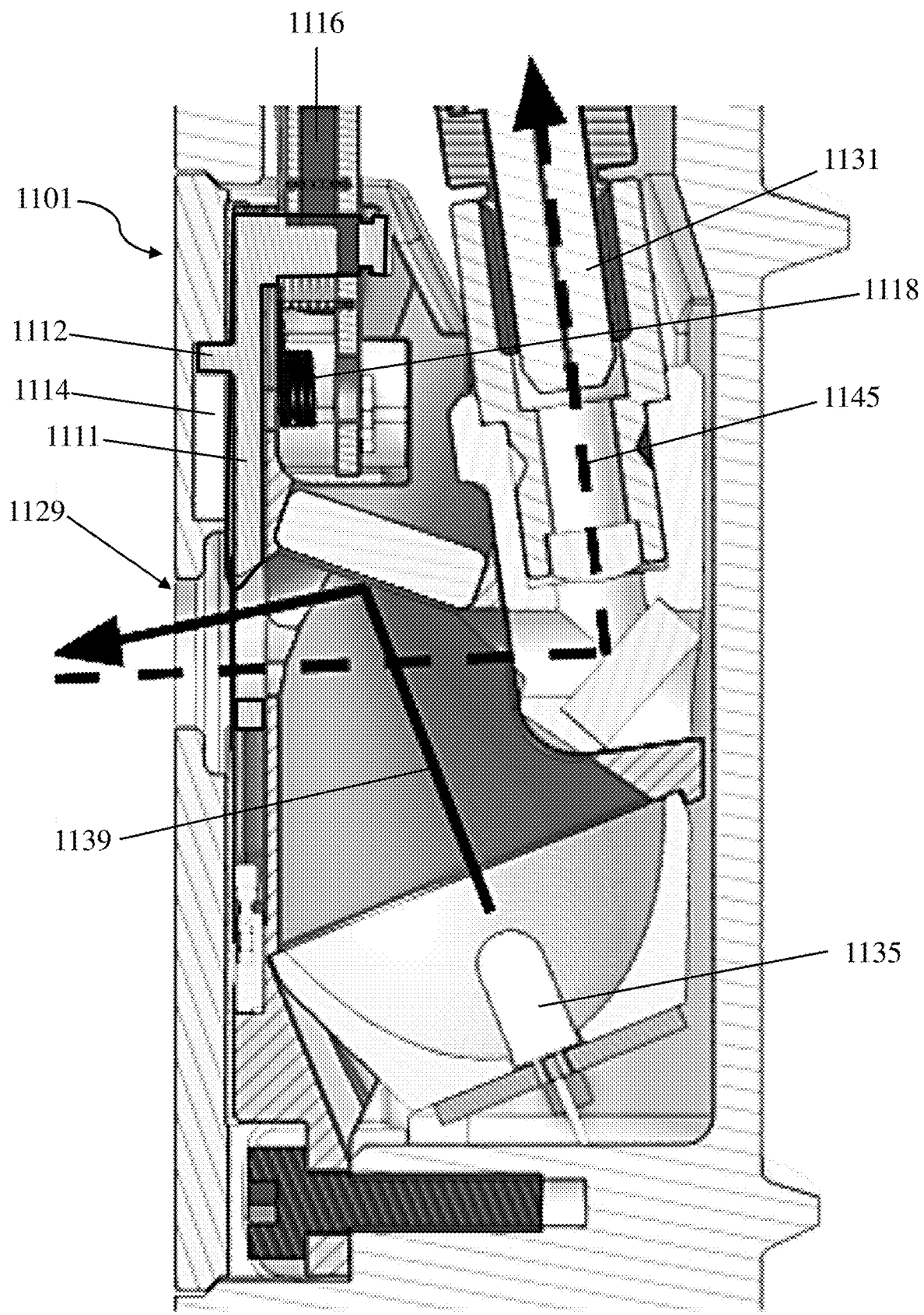
FIG. 4A presents a cross-sectional schematic illustration of an exemplary rotational soil penetrometer head comprising an optics module, according to some embodiments.
Figure 4B:
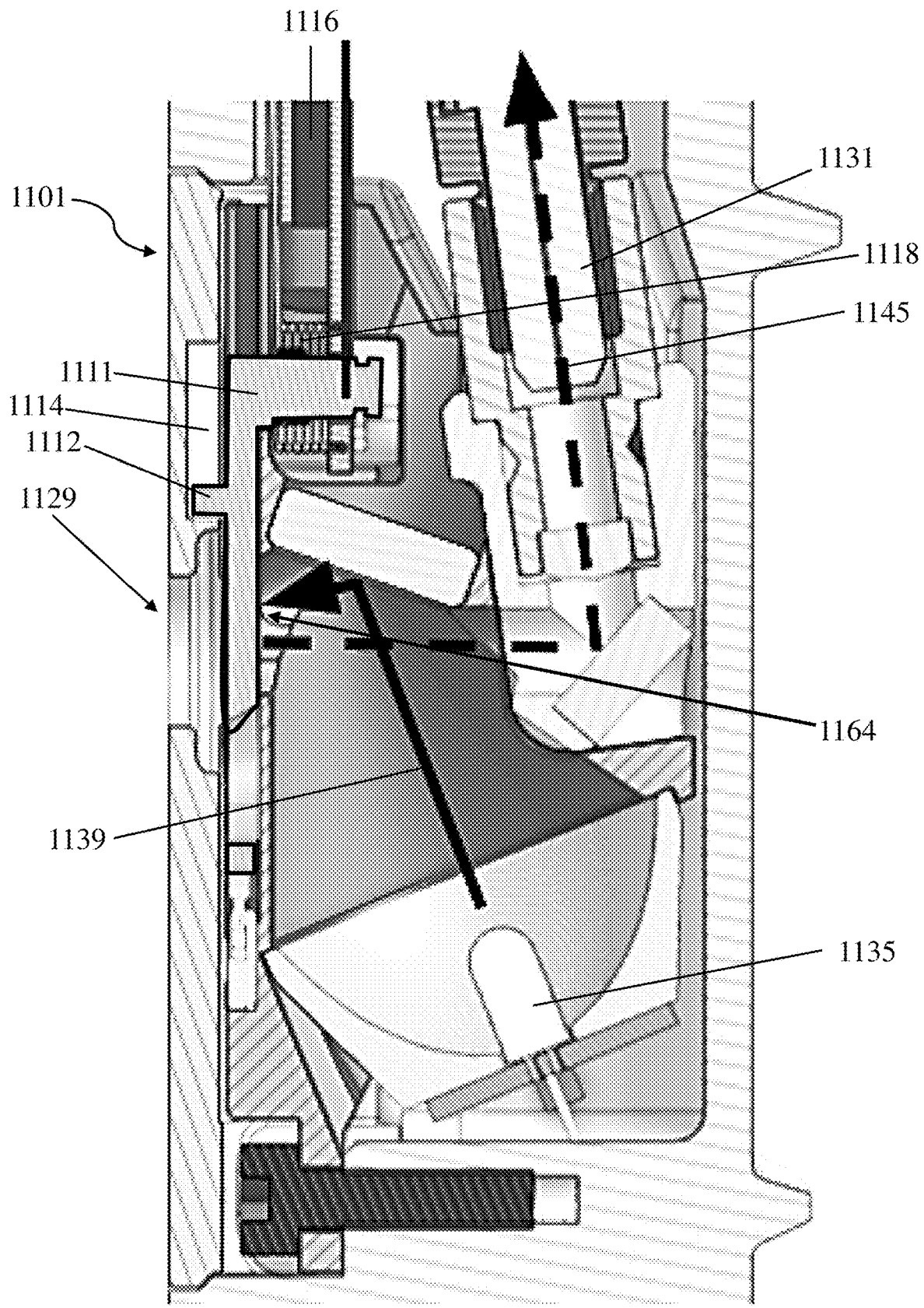
FIG. 4B presents a cross-sectional schematic illustration of an exemplary rotational soil penetrometer head comprising an optics module, according to some embodiments.
Figure 4C:
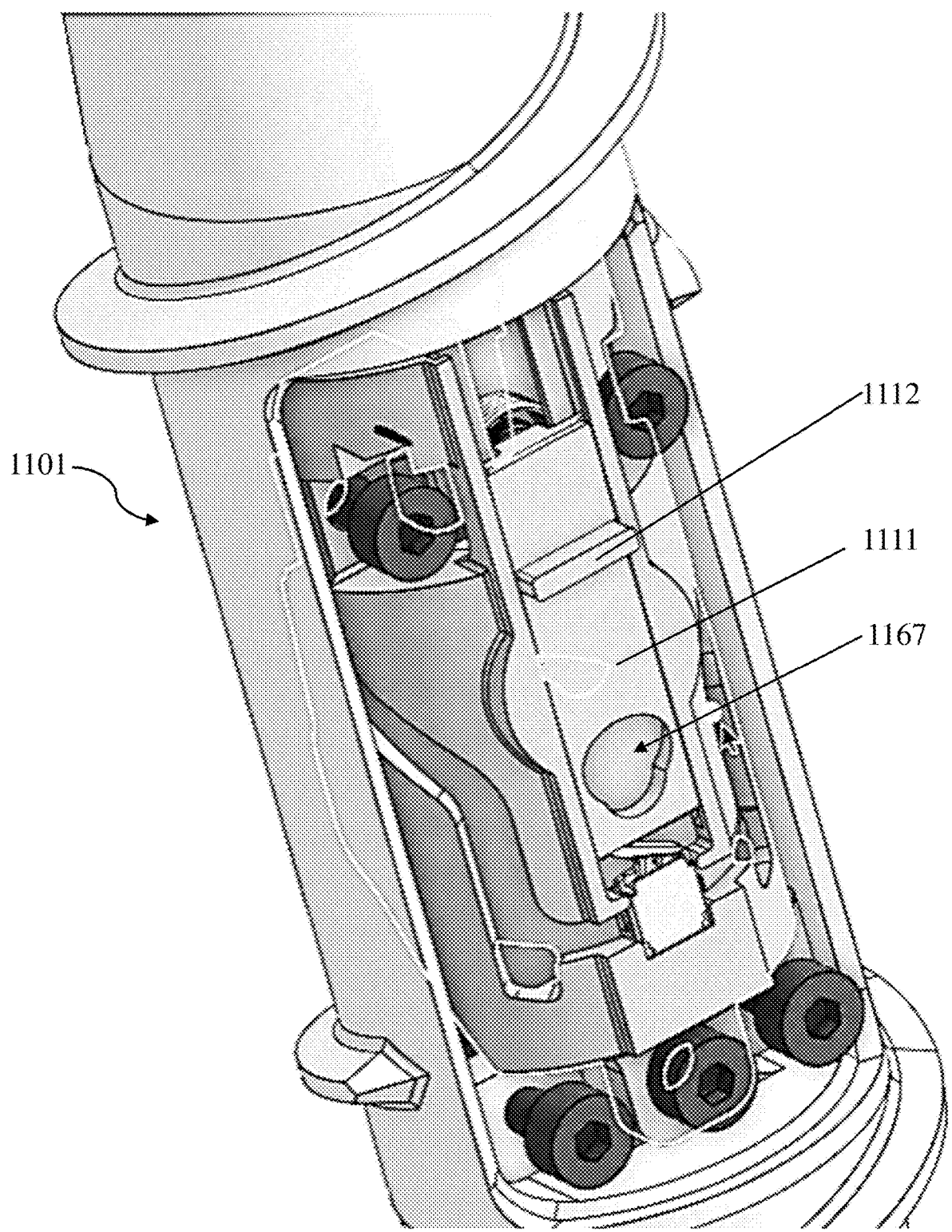
FIG. 4C presents a perspective schematic illustration of an exemplary rotational soil penetrometer head comprising an optics module, according to some embodiments.

The penetrometer may comprise one or more components to control and/or calibrate the spectrometer, which are used for improving the accuracy of spectroscopic measurements, according to some embodiments. For example, the penetrometer may comprise a calibration shutter, according to some embodiments. The optics module may include the shutter, according to some embodiments. For example, FIGS. 4A-4C present schematic illustrations of a non-limiting optics module of penetrometer 1101 comprising shutter 1111, according to some embodiments. FIG. 4A presents a schematic, cross-sectional illustration of penetrometer 1101, where shutter 1111 is in an open position, such that light 1139 emitted from light source 1135 can be transmitted through a hole (e.g., hole 1167 shown later, in FIG. 4C) formed in the shutter 1111 through exposed window 1129 when the hole and window are aligned, and such that signal (e.g., light reflected from the penetrometer surroundings and through window 1129) can be transmitted along path 1145, traveling along optical fibers 1131 to a spectrometer (not shown). Thus, when shutter 1111 is in the open configuration, penetrometer 1101 comprises an optics module very similar to the optics module described with reference to FIG. 3, above.

However, in some embodiments, shutter 1111 may be in the closed position. For example, FIG. 4B is similar to FIG. 4A, but shows shutter 1111 in the closed position. When shutter 1111 is in the closed position, any light 1139 produced by light source 1135 is blocked by shutter 1111 when an associated hole (e.g., hole 1167, shown later, in FIG. 4C) formed in the shutter is misaligned with window 1129 such that window 1129 is blocked, and any light sent along optical fibers (e.g., along path 1145) is reflected off of an interior surface of the shutter 1111 itself, rather than from the surroundings of the penetrometer.

The shutter itself may be manually actuated (e.g., switched between a closed configuration and an open configuration), or may be coupled to a shutter actuator that actuate the shutter automatically. For example, referring again to FIGS. 4A-4B, shutter 1111 is configured to be slidingly coupled to grooves of the interior wall of the optics module (the grooves cannot be seen in these cross-sections), within which shutter 1111 can slide vertically in response to an action by the shutter actuator, though other moveable mechanical attachments may also be used. The shutter actuator may move the shutter by any of a variety of methods known to those of ordinary skill in the art. For example, the shutter actuator may be connected to a motor configured to slide the shutter within the groove. Alternatively, a shutter may be actuated by using a magnetic solenoid to pull on a cable connected to the shutter. For example in FIG. 4A, shutter 1111 is connected to cable 1116. The cable can be configured to pull on the shutter and to be actuated by a magnetic solenoid shutter actuator in a separate portion of the penetrometer. A shutter may be biased towards a particular configuration (e.g., a closed configuration or an open configuration) using a spring, such that in the absence of action by the shutter actuator, the shutter remains in the configuration towards which the spring biases it. Referring again to FIG. 4A, for example, shutter 1111 is connected to torque spring 1118, which is configured to bias shutter 1111 towards a closed configuration. For example, in some embodiments, a magnetic actuator can actively maintain the shutter in an open configuration until it is turned off, at which point, a spring connected to the shutter will bias it towards the closed configuration. In the open configuration shown in FIG. 4A, cable 1116 has been actuated by a magnetic solenoid (not shown) that has forced spring 1118 into a stressed configuration. However, in FIG. 4B, the magnetic solenoid has not been actuated, allowing spring 1118 to pull shutter 1111 and cable 1116 until shutter 1111 is in the closed configuration, shown. The shutter actuator (e.g., the magnetic actuator or motor) may be located in any of a variety of appropriate portions of the penetrometer, such as the penetrometer head or within a housing attached to a proximal portion of the shaft opposite the penetrometer head.

In some embodiments, the shutter comprises a hard-stop, configured to constrain the shutter to a safe position. For example, in FIGS. 4A-4B, shutter 1111 comprises lip 1112 configured to slide within grove 1114. As shown in FIGS. 4A-4B, the hard-stop may act as a physical limit on the position of the shutter, which helps to maintain the shutter in an appropriate configuration if the shutter actuator applies an excessive force to the shutter. Although a lip and groove hard-stop is shown, any of a variety of appropriate hard stops may be used, as the disclosure is not so limited.

A shutter actuator may be connected to other electronic components (e.g., a processor, as described in greater detail below), such that in response to processor instructions, the shutter actuator can actuate shutter 1111, thereby actuating shutter 1111 between the open configuration shown in FIG. 4A and the closed configuration shown in FIG. 4B. Of course, while a single mode of shutter actuation is shown in FIGS. 4A-4B, it should be understood that other shutter configurations (e.g., wherein the shutter is actuated by rotational motion) and modes of actuation are also possible as the disclosure is not so limited.

FIG. 4C shows a perspective, schematic illustration of shutter 1111 within penetrometer 1101, where a portion of penetrometer 1101 has been hidden to permit visual inspection of shutter 1111. As shown, shutter 1111 comprises hole 1167 that can be sized and shaped to at least partially align with a window of the penetrometer (not shown) when shutter 1111 is in the open configuration, and which is misaligned with the window when shutter 1111 is in the closed configuration.

As noted above, in some embodiments, a shutter may be used to calibrate a soil penetrometer. In such an embodiment, at least a portion of a shutter, such as calibration surface 1164 of shutter 1111 (shown in FIG. 4B), positioned within a field of view of optical fibers 1131, may comprise a reference material with a known response to illumination by light source 1135. Thus, the shutter may be used to calibrate the spectrometer by transmitting a reference signal to the spectrometer (e.g., along path 1145 of FIG. 4B) when illuminated. However, the various embodiments disclosed herein are not limited to using shutters for calibration purposes. For example, the use of shutters comprising spectroscopically inert materials is also contemplated.

Any of a variety of methods may be used to calibrate the spectrometer using the shutter, and useful calibration protocols may be identified by those of ordinary skill in the art. Calibration may be based at least in part on a measured calibration signal from a calibration surface of the shutter when the shutter is in the closed configuration. The resulting calibration may be used to correct subsequent measurements by the spectrometer. In some embodiments, the calibration may also be based at least in part on a dark signal which may correspond to a signal collected by the spectrometer while the shutter is in the closed configuration and the light source is off.

The above noted calibration process may be performed manually, or may be performed as part of an automatic process regulated by the penetrometer. In some embodiments, the spectrometer is calibrated at the beginning and the end of each soil penetration, to ensure that calibration did not change over the course of the measurement. For example, a calibration measurement may be performed prior to soil insertion and after collecting information related to a specific sample location. According to other embodiments, high-accuracy calibrations are performed occasionally, as a part of routine maintenance of the spectrometer.

In some embodiments, the optics module may be at least partially removable. For example, referring to FIG. 3, in some embodiments external panel 270 and window 229 may be selectively removable. Additionally, in some instances one or more other components of the optics module may either be included in a single removable unit and/or they may be individually positioned within the cavity. For example, in one specific embodiment, the various optical components of an optics module shown disposed in the cavity (e.g., the light source 227, illumination mirror 236, illumination mirror 237, mirror 233, and lens 234) may be integrated into a single body that may be selectively inserted into and removed from the cavity together. The one or more optical fibers 231 may be selectively connected to a corresponding connector on the optics module to facilitate assembly and connection of the spectrometer with the removable optics module. Alternatively, embodiments in which these various components are permanently affixed within the cavity of the rotational soil penetrometer are also contemplated as the disclosure is not limited in this fashion.

In some embodiments, the cavity and/or optics module of the rotational soil penetrometer is both axially and rotationally fixed to the head. Thus, optics module 227 of FIGS. 2A-3 is configured to rotate along with head 203 of the rotational soil penetrometer as the head is rotated into the soil. Rotation of the optics module may, advantageously, mitigate the possibility of soil becoming stuck to the window of the optics module, thereby improving the quality of spectroscopic data.

The optical fiber may extend along the shaft of the rotational soil penetrometer. For example, referring again to FIG. 1A, the optical fiber extends through a hollow interior of the shaft 113. As illustrated in FIG. 1A, the optical fiber within shaft 113 may optically connect a spectrometer 117 to cavity 111. Thus, spectrometer 117 may be operatively coupled to optics module 127 once it is received by cavity 111. Any appropriate type of spectrometer may be used. For example, the spectrometer may be configured to measure wavelengths as described above. In some embodiments, the spectrometer is mechanically coupled to the rotational soil penetrometer. This spectrometer placement may be advantageous, because it allows the spectrometer to rotate with the rotational soil penetrometer, thereby preventing twisting of the optical fiber connecting the spectrometer to the optics module during use. However, it should be understood that other placements of the spectrometer are envisioned, such as placement of the spectrometer in the head, and/or placement of the spectrometer external to the rotational soil penetrometer, as the disclosure is not so limited.

The spectrometer itself may operate in any of a variety of appropriate modes. For example, in some embodiments, the spectrometer is a single-range spectrometer, but in some embodiments the spectrometer is a multi-range spectrometer, including multiple detection mechanisms configured to detect signal from different portions of the electromagnetic spectrum. Multi-range spectrometers may accomplish the detection at different ranges using any of a variety of appropriate methods. For example, the spectrometer may comprise multiple detectors, light splitters, and/or any of a variety of other optical components suitable for use in a spectrometer. In some embodiments, multi-stage spectrometers may be advantageous, since they can extend the overall range of the electromagnetic spectrum which the spectrometer may detect.

Figure 5:
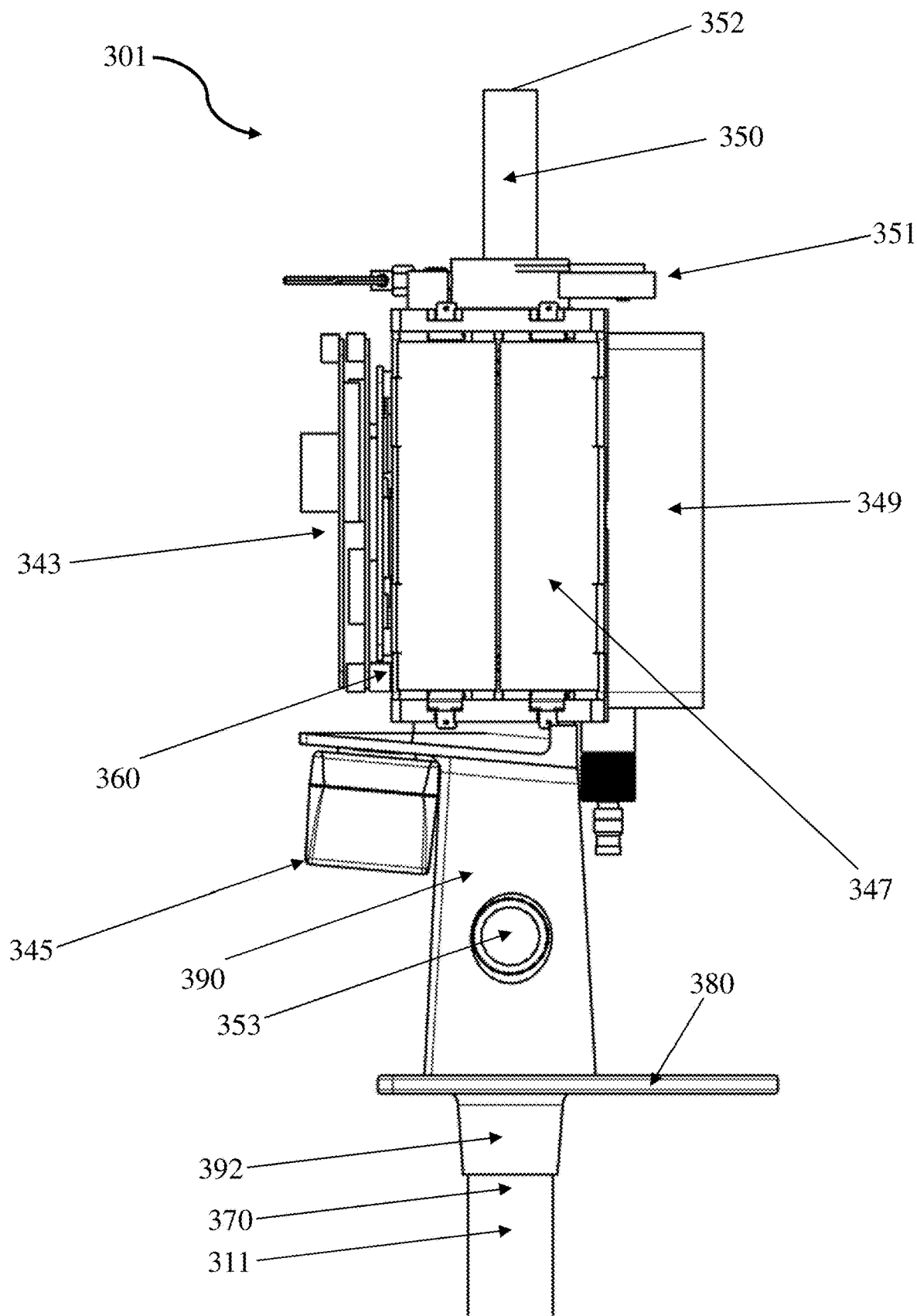
FIG. 5 presents a side-view schematic illustration of an interior of a proximal portion of an exemplary rotational soil penetrometer, according to some embodiments.

In some embodiments, the rotational soil penetrometer comprises a bracket configured to connect the associated shaft and head to one or more proximal components of the system. The bracket may be fixed to the shaft, in some embodiments. However, in some embodiments, the bracket is coupled to the shaft via one or more intervening parts. For example, the bracket may be coupled to the shaft by being fixed to a distal housing component fixed to the shaft. FIG. 5 presents a side view schematic illustration of a bracket 360 fixed to a distal portion of a housing 390 of rotational soil penetrometer 301, in some embodiments.

In some embodiments, the bracket is surrounded by a housing. However, other arrangements can be used. For example, rather than a bracket, the rotational soil penetrometer may comprise a structural housing configured to connect the shaft and the one or more proximal components of the rotational soil penetrometer without requiring a separate bracket as the disclosure is not so limited.

In some embodiments, rotational soil penetrometer comprises a housing configured to surround the bracket. The housing is configured to protect delicate components of the rotational soil penetrometer from impact (e.g., during rotation of the rotational soil penetrometer). In some embodiments, the housing is configured to protect delicate components of the rotational soil penetrometer from soiling, (e.g., during operation of the rotational soil penetrometer). The housing may be integrally formed with the bracket, or may be a separate component.

As shown in FIG. 5, according to some embodiments, the distal portion of the housing 390, or other component, is fixed to proximal end portion 370 of shaft 311 of rotational soil penetrometer 301 at connection 392. Appropriate connections may include press fits, welds, fasteners, pins, and/or any other appropriate type of connection. In some embodiments, the bracket is configured to connect the shaft and head to one or more proximal components of the system. For example, the bracket may be used to mount the spectrometer on the rotational soil penetrometer, in some embodiments. The bracket may be mechanically coupled to the shaft of the rotational soil penetrometer (e.g., mechanically coupled to a proximal end portion of the shaft of the rotational soil penetrometer).

Figure 8:
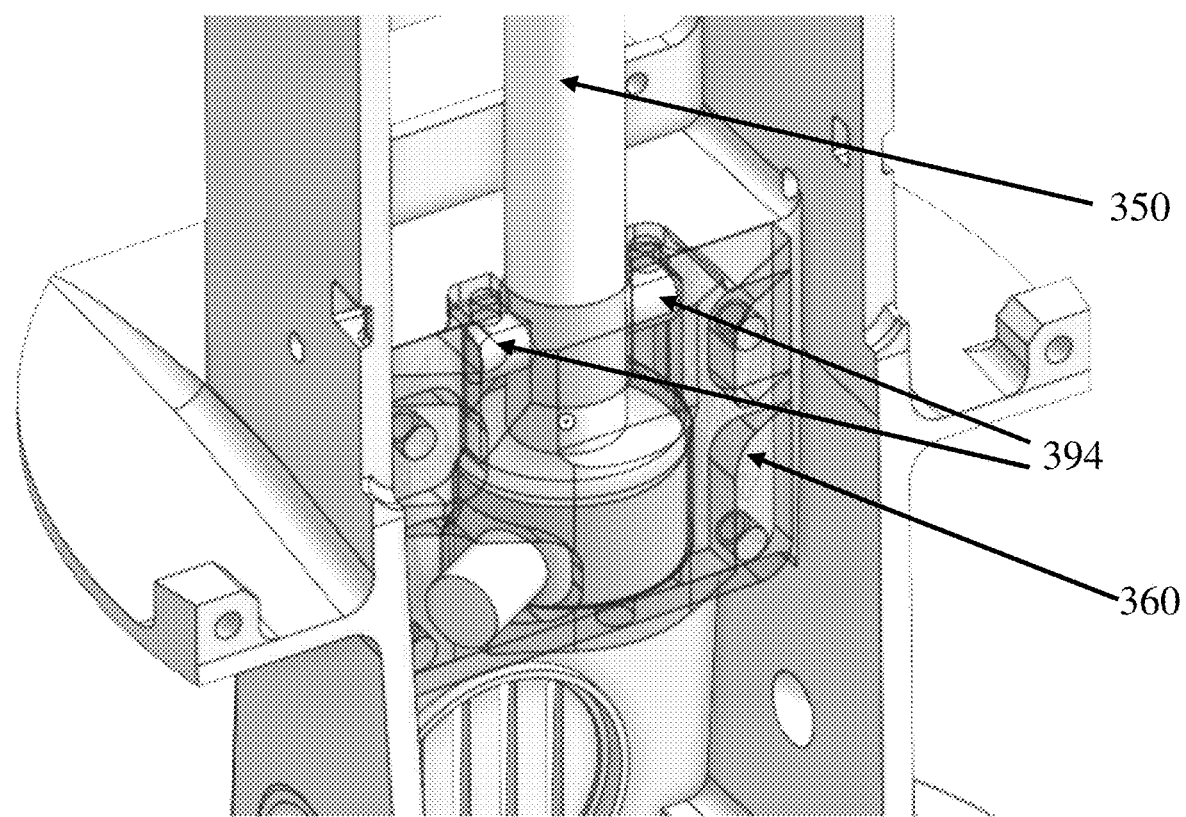
FIG. 8 presents a cross-section of an exemplary rotational soil penetrometer, according to some embodiments.

A spectrometer 349 is mounted on bracket 360, in some embodiments, as shown in FIG. 5. The bracket 360 is both axially and rotationally fixed to the shaft 311 via the distal portion of the housing 390, though embodiments in which a direct connection between the bracket and shaft is used are also contemplated. In either case, rotation of the bracket and other associated components with the shaft may advantageously allow rotation of the spectrometer along with the head, reducing the risk of twisting or damaging of an optical fiber or other components extending between the various portions of the rotational soil penetrometer. In some embodiments, the bracket is mechanically coupled to a driveshaft extending proximally outwards from the bracket and body. The driveshaft may be configured to operatively couple to a drive system. For example, FIG. 8 presents bracket 360 that is mechanically coupled to driveshaft 350, which is configured to operatively couple at proximal end portion 352 of driveshaft 350 to a drive system (not pictured in FIG. 8, but previously pictured in FIGS. 5-6), according to some embodiments.

Figure 6:
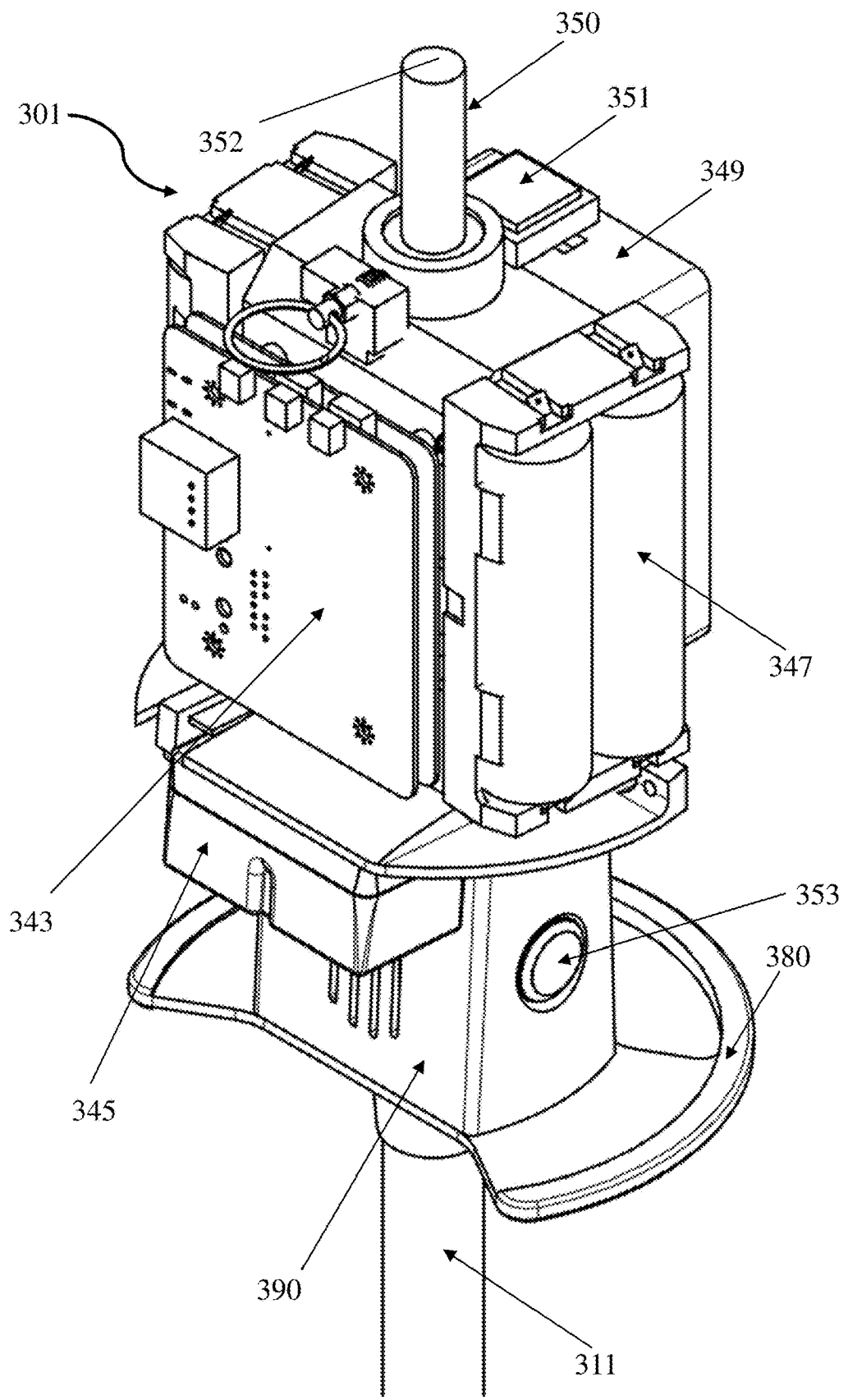
FIG. 6 presents a perspective-view schematic illustration of an interior of a proximal portion of an exemplary rotational soil penetrometer, according to some embodiments.

The rotational soil penetrometer may comprise a switch 353 as shown in FIGS. 5-6, which may be positioned on any appropriate portion of a housing or other part of the penetrometer. The switch may be operatively coupled to one or more components of the rotational soil penetrometer. For example, the switch may be operatively coupled to the spectrometer of the rotational soil penetrometer. The switch may be used to control the operation of the spectrometer, in some embodiments. For example, the switch may be configured to switch the spectrometer, as well as other sensors and components, between a collection mode and a standby or off mode, in some embodiments. According to certain embodiments, the switch may be configured to turn the spectrometer, as well as other sensors and components, on or off.

Other rotational soil penetrometer components may be mounted on the bracket. For example, in some embodiments, a power supply is mounted on the bracket. Returning to the example of FIG. 5, a power supply 347 is mounted to bracket 360. The power supply may be one or more batteries, as illustrated in the example of FIG. 5, but one of ordinary skill would understand that any of a variety of suitable power supplies may be used for the rotational soil penetrometer. For example, the rotational soil penetrometer may comprise a super capacitor, or a connection to an external power source, such as a generator, outlet, or other appropriate power supply, as the disclosure is not so limited.

In some embodiments, the rotational soil penetrometer comprises a GNSS antenna as described above. The GNSS antenna may be mounted on the bracket, in some embodiments. For example, FIG. 5 presents a GNSS antenna 351, which is mounted on bracket 360 of rotational soil penetrometer 301, in some embodiments. However, embodiments, in which the antenna is mounted on other portions of the penetrometer including the penetrometer housing are also contemplated. Additionally, embodiments in which other localization systems are used, as well as embodiments in which no localization system is used, are also contemplated.

The rotational soil penetrometer may comprise electronics. With reference to FIG. 5, rotational soil penetrometer 301 comprises electronics 343, in some embodiments. The electronics may serve a variety of operative functions within the rotational soil penetrometer. For example, in some embodiments, the electronics comprise one or more processors. The electronics may comprise a computer readable storage medium operatively coupled to the one or more processors, as described below. The inclusion of the computer readable storage medium may allow storage of soil data recorded by the rotational soil penetrometer and may include processor executable instructions that when executed by the one or more processors perform any of the methods described herein. The data may be collected by the spectrometer, or by any of a variety of other sensors (e.g., a depth sensor, a penetration torque sensor, a penetration force sensor) described in greater detail below. Additionally or alternatively, in some embodiments the electronics may comprise a wireless transmitter configured to communicate wireless using any appropriate wireless communication protocol (e.g., WiFi, radio, cellular, Bluetooth, etc.). For example, the transmitter may be configured to transmit data from the rotational soil penetrometer to a computing device (e.g., a computer, a server comprising a database, or a mobile device such as a cell phone), though wired connections may also be used. In some embodiments, the electronics are electrically connected to the power supply. The electronics may also be connected to the spectrometer, and/or one or more additional sensors of the rotational soil penetrometer as described in greater detail below.

According to certain embodiments, the rotational soil penetrometer also comprises a depth sensor. The depth sensor may be configured to measure a distance between a proximal end of the shaft corresponding to an end of a portion of the shaft intended to be inserted into soil and a surface of the soil. For example, referring again to FIG. 5, rotational soil penetrometer 301 comprises a distance sensor 345, which is configured to measure the distance between the sensor and the surface of soil into which the head of the rotational soil penetrometer has been inserted. According to certain embodiments, the depth sensor may be used to determine a penetration depth of the optics module. The penetration depth of the optics module may be determined by subtracting the distance between the depth sensor and the soil surface from the known distance between the depth sensor and the optics module. Similarly, in some embodiments, the depth sensor may be used to determine a penetration depth of the distal end portion of the head. The penetration depth of the distal end portion of the head may be determined by subtracting the distance between the depth sensor and the soil surface from the known distance between the depth sensor and the distal end portion of the head. of a variety of appropriate types of depth sensor may be used.

For instance, the distance sensor may be an optical distance sensor, such as an infrared or laser distance sensor. In some embodiments, the depth sensor is an ultrasonic distance sensor, as the disclosure is not so limited. It has been recognized that the use of an ultrasonic distance sensor may be particularly advantageous, since the accuracy of ultrasonic distance sensors is unaffected by environmental lighting conditions which is contrasted with the sensitivity of infrared and laser distance sensors to changes in environmental lighting conditions.

The use of a rotational soil penetrometer comprising two or more depth sensors is also possible, and may present a number of advantages. For example, in some embodiments, depth measurements of a depth sensor may be intermittent or otherwise compromised (e.g., by bright daylight, tall vegetation, signal loss, and other potential interference), which can result in reduced accuracy of the depth measurements. However, when multiple depth sensors are used, (e.g., a first depth sensor on a first portion of the penetrometer and a second depth sensor on a second portion of the penetrometer) a composite depth may be determined by combining the independent measurements of the depth sensors. The composite depth may be determined in any of a variety of ways known to those of ordinary skill in the art. For example, the composite depth may be measured as the maximum depth observed by either sensor, or may be an average of the depth measurements made by the sensors, combinations of the forgoing, and/or any other appropriate method of determining the depth. An appropriate method of determining composite depth may be selected based on ambient conditions of the penetrometer, as well as based on the kind of depth sensor used (e.g., an ultrasonic distance sensor which may also be referred to as an ultrasound distance sensor, an infrared distance sensor, or a laser distance sensor), in a way that will produce an accurate depth measurement, according to some embodiments.

In some embodiments, the penetration of the rotational soil penetrometer into the soil is limited by a guard plate (e.g., of the distal housing component). For example, referring to FIG. 5, penetration of rotational soil penetrometer 301 is limited by guard plate 380 that is attached to a proximal portion of the shaft 311. Thus, the guard plate may stop further penetration of the penetrometer into the ground upon contact with the ground. Separately, in some embodiments the guard plate may be offset from, include a cut out, or otherwise be configured to provide clearance for a field of view of the distance sensor 345 to permit distance measurements to be collected even while providing the desired functionality of stopping further penetration of the shaft beyond a predetermined distance.

Figure 7:
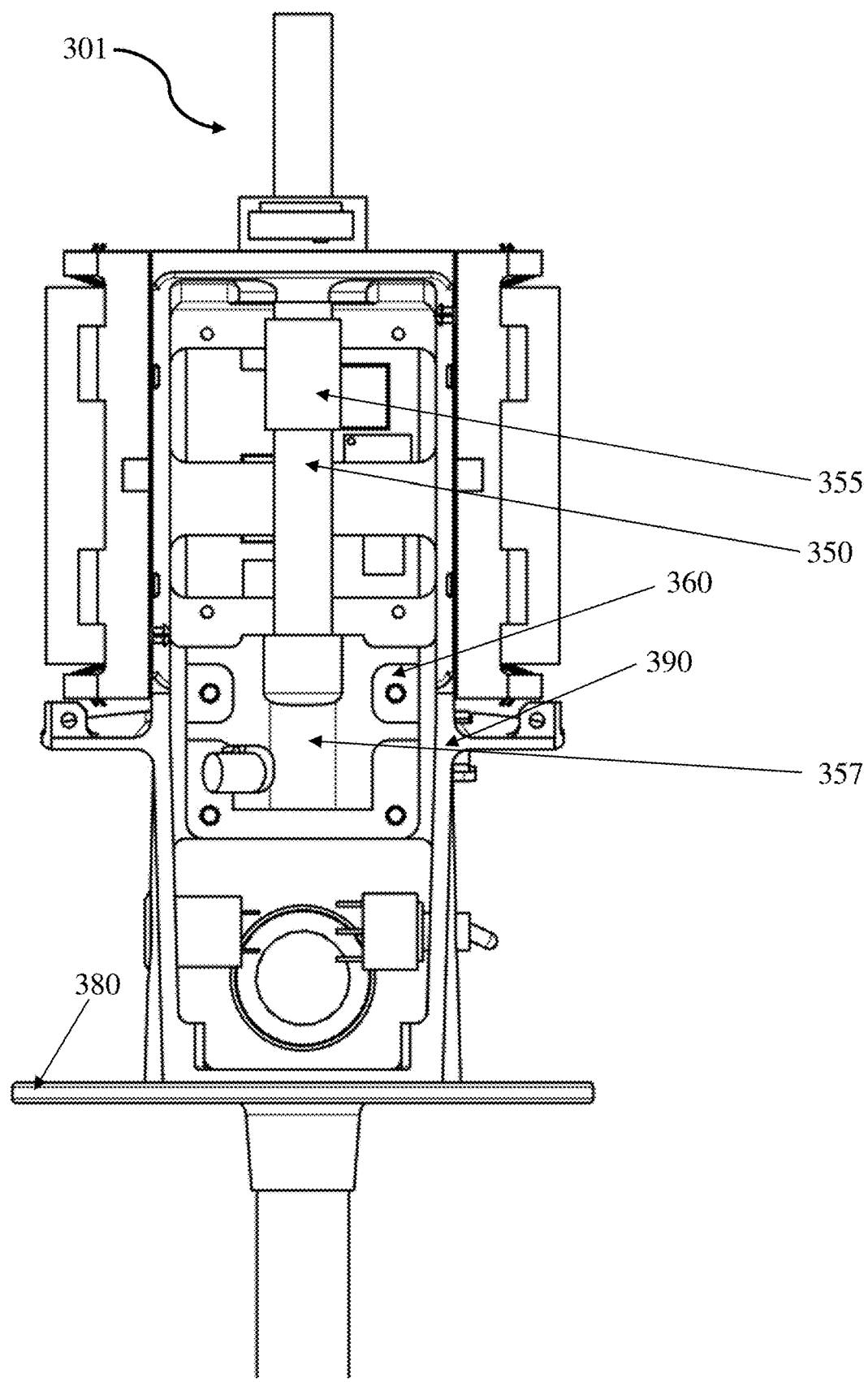
FIG. 7 presents a front-view schematic illustration of an exemplary rotational soil penetrometer comprising a torque sensor and a force sensor, according to some embodiments.

As noted above, the rotational soil penetrometer may include a drive shaft operatively coupled to the shaft. For example, FIGS. 5-8 present exemplary rotational soil penetrometer 301 wherein shaft 311 is operatively coupled to a driveshaft 350 via a housing and/or bracket. For example, as shown in FIG. 7, drive shaft 350 may extend into and be rotationally and axially fixed with the bracket 360.

In some embodiments, the rotational soil penetrometer comprises load sensors. The load sensors may be configured to collect mechanical soil data as described above. FIG. 8 presents a cross-sectional schematic illustration of the rotational soil penetrometer 301 shown in FIGS. 5-7, illustrating load sensors 355 and 357 of the rotational soil penetrometer. In some embodiments, the load sensor is a torque sensor. For example, sensor 355 is a torque sensor configured to measure a penetration torque applied about a longitudinal axis of the shaft of the penetrometer. According to some embodiments, the load sensor is a force sensor. For example, sensor 357 is a force sensor configured to measure penetration force applied to the shaft of the penetrometer, in some embodiments. Embodiments in which both sensors are used are also contemplated. For example, a penetrometer may comprise two load sensors (a force sensor and a torque sensor), or may comprise a single load sensor that is configured to measure both force and torque. In some embodiments, the load sensor (e.g., the force sensor; the torque sensor) is operatively coupled to the electronics of the rotational soil penetrometer. For example, the load sensor may be operatively coupled to a processor of the rotational soil penetrometer. Thus, the load sensor may transmit sensed mechanical data to the electronics, in some embodiments. In some embodiments, the load sensor may be controlled, and data from the load sensor may be logged.

A torque sensor may be configured to measure a penetration torque associated with the head. For example, the torque sensor may be configured to detect penetration torque produced by friction of the head in the soil, and transmitted along the shaft. The torque sensor of the rotational soil penetrometer may be any of a variety of appropriate torque sensors. For example, the torque sensor may be a strain gauge attached to the shaft or the driveshaft such that the strain gauge may detect penetration torque by measuring deformation of the shaft or the driveshaft resulting from the application of the penetration torque on the shaft by the head of the rotational soil penetrometer. Alternatively, the torque sensor may be a separate sensors attached to the shaft and/or the drive-shaft, disposed along a force path joining the shaft and the associated driveshaft, in a drive mechanism (e.g., an applied motor torque), and/or any other appropriate sensor configuration. For example, torque sensor 355 may be mechanically coupled between bracket 360 and driveshaft 350 of rotational soil penetrometer 301, as shown in FIG. 8. In some embodiments, the rotational soil penetrometer is configured such that a large portion of the penetration torque detected by the torque sensor arises from penetration torque acting on the head of the rotational soil penetrometer. For example, in some embodiments, greater than or equal to 30%, greater than or equal to 40%, greater than or equal to 50%, greater than or equal to 60%, greater than or equal to 70%, greater than or equal to 80%, greater than or equal to 90%, or more of the penetration torque detected by the torque sensor arises from penetration torque acting on the head. In some embodiments, less than or equal to 100%, less than or equal to 90%, less than or equal to 80%, less than or equal to 70%, or less of the torque detected by the torque sensor arises from torque acting on the head. Combinations of these ranges are possible. For example, in some embodiments, greater than or equal to 30% and less than or equal to 100% of the penetration torque detected by the torque sensor arises from penetration torque acting on the head.

As noted above, a rotational soil penetrometer may comprise a linear force sensor, in some embodiments. The force sensor may be configured to measure a penetration force associated with the head. For example, the load sensor may be configured to detect a penetration force acting on a distal end of the head. The force sensor of the rotational soil penetrometer may be any of a variety of appropriate force sensors including a load cell, a strain gauge, an extensometer, or any other appropriate linear force sensor. The force sensor may be mechanically coupled to the bracket, in some embodiments. For example, force sensor 357 of FIG. 7 is mechanically coupled to the bracket of rotational soil penetrometer 301, as described above, such that linear force may be transmitted along a force path from the drive-shaft, through the force sensor, to the bracket, to the shaft, and ultimately, to the head of the penetrometer. For example, in some embodiments, an internal end of the drive-shaft is configured to compress a force sensor (e.g., a load cell). Specifically, driveshaft 350 in FIG. 7 is configured to compress force sensor 357 disposed axially in-line with the driveshaft such than an axial force applied to the driveshaft is transmitted to the force senor. The force sensor may be axially fixed to the bracket or housing such that linear force applied by the drive-shaft is transferred to the shaft and head. However, instances in which other force sensor arrangements and/or other housing configurations are used are also contemplated, as the disclosure is not so limited.

FIG. 8 presents a cross-section of the rotational soil penetrometer according to certain embodiments, wherein bracket 360 is partially transparent. As shown in the figure, driveshaft 350 may be rotationally fixed to the bracket by a pin joint 394 for transmitting a torque to the bracket 360 or housing of a penetrometer. However, other types of connections for rotationally fixing the driveshaft to the bracket and/or housing are also contemplated.

While a specific arrangement for a driveshaft is described above and in the figures, any of a variety of appropriate drive shaft configurations may be used. Additionally, while the depicted driveshaft is configured to be selectively removable from a drive system permanently attached drive systems are also contemplated. Further, depending on the embodiment, and as described further below, the drive system is used with the depicted driveshaft may either be hand-held drive systems, such as a hand-held drilling device, portable stand alone systems, and/or vehicle mounted systems as the disclosure is not so limited.

Figure 9:
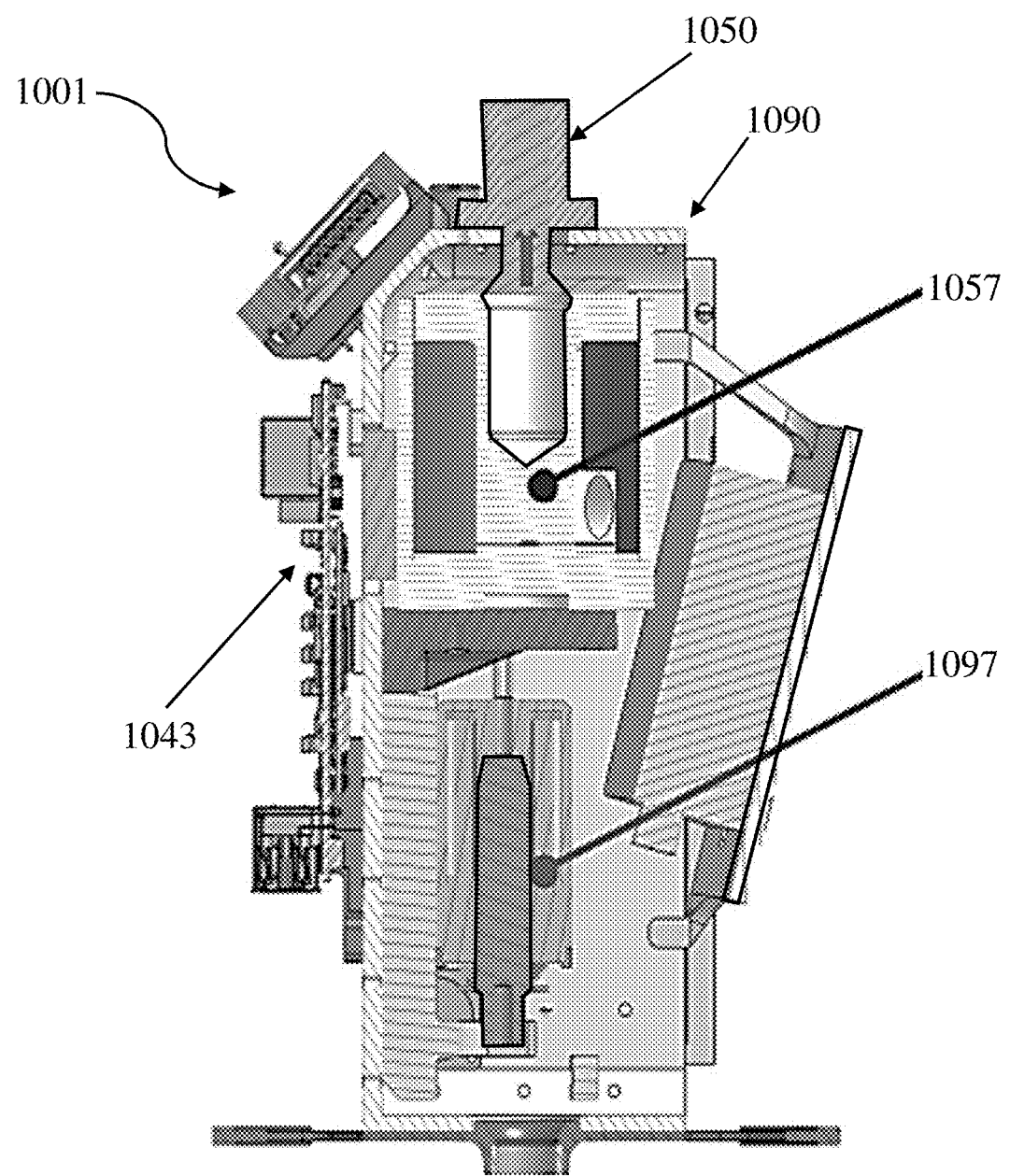
FIG. 9 presents a cross-sectional schematic illustration of an exemplary rotational soil penetrometer comprising a load sensor that is both a force sensor and a torque sensor, according to some embodiments.

FIG. 9 presents a cross-sectional schematic illustration of a non-limiting rotational soil penetrometer 1001 similar to rotational soil penetrometer 301 of FIGS. 5-8 but including a single load sensor 1057 that is configured to function simultaneously as a force sensor and a torque sensor. Penetrometer 1001 comprises drive shaft 1050 that extends into load sensor 1057, which is axially and rotationally fixed to housing 1090. One advantage of using monolithic load sensor 1057 is that a bracket is no longer necessary to couple the drive-shaft to the housing; load sensor 1057 is directly connected to housing 1090. Monolithic load sensor 1057 may connected to housing 1090 in any of a variety of ways known to those of ordinary skill in the art (e.g., by an adhesive, a mechanical fastener, mechanical interlocking features, welds, and/or any other appropriate type of connection). Similarly, monolithic load sensor 1057 may be connected to drive shaft 1050 in any of a variety of ways known to those of ordinary skill in the art (e.g., by an adhesive, a mechanical fastener, mechanical interlocking features, welds, and/or any other appropriate type of connection). Penetrometer 1001 further comprises electronics 1043 (similar to electronics 343 of penetrometer 301 in FIGS. 5-8), and further comprises shutter actuator 1097 suitable for operation of a shutter (e.g., shutter 1111 of FIGS. 4A-4C), but these components are not strictly necessary as FIG. 9 is a non-limiting example. Shutter actuator 1097 may be electrically connected to electronics 1043, such that a processor included in electronics 1043 can provide an instruction to actuate a motor (not shown) that controls a shutter of the penetrometer (not shown) as discussed in greater detail above.

Figure 10:
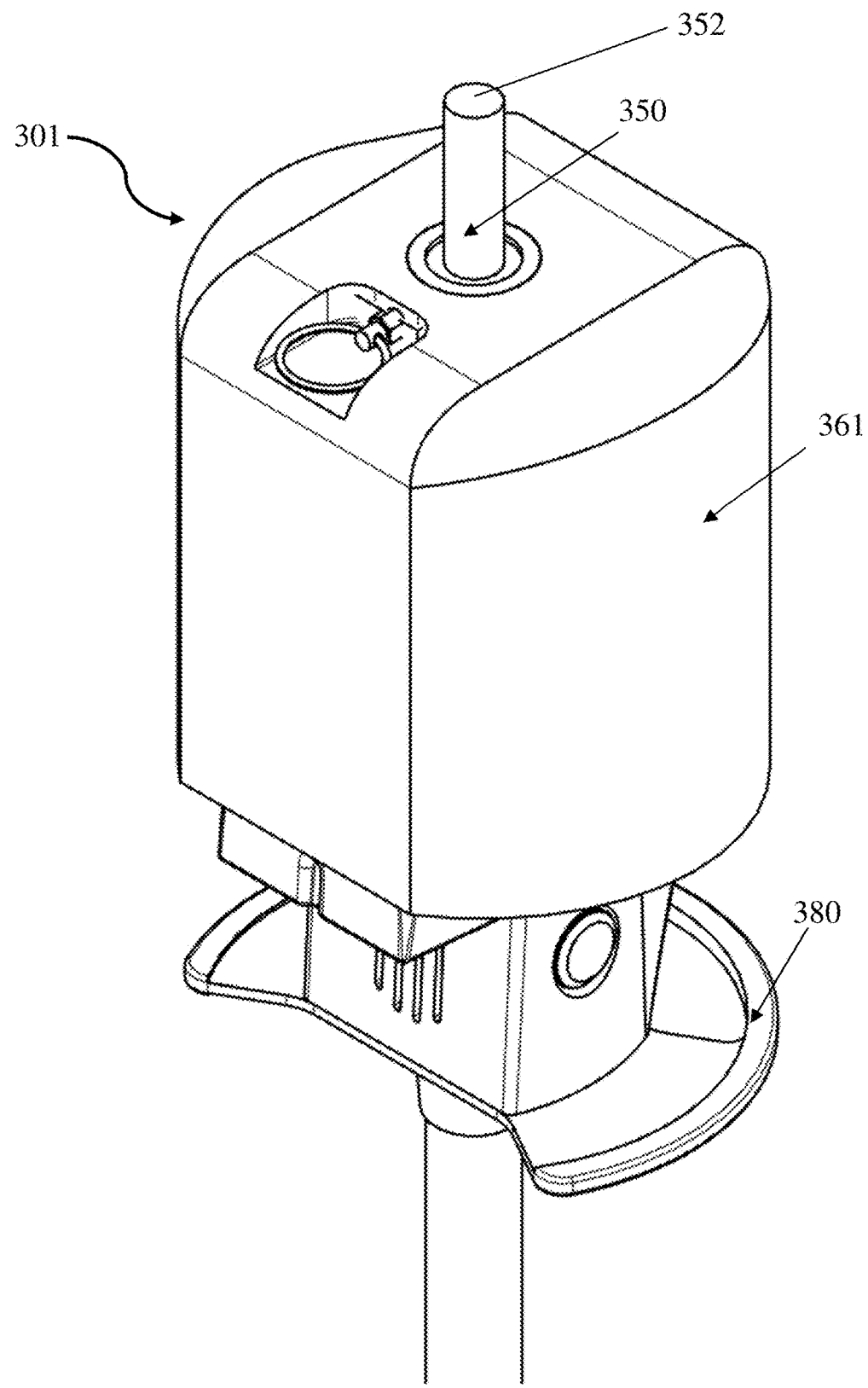
FIG. 10 presents a perspective-view schematic illustration of a proximal portion of an exemplary rotational soil penetrometer, according to some embodiments.

FIG. 10 presents a perspective, schematic illustration of the rotational soil penetrometer 301 in the same orientation as FIG. 6, wherein the bracket, spectrometer, and electronics have been surrounded by a housing 361, as described in greater detail above.

Figure 11A:
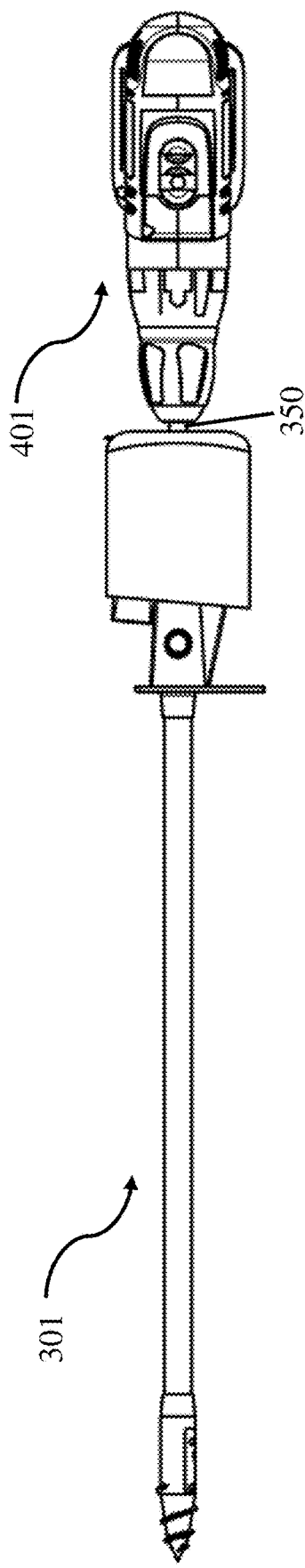
FIG. 11A presents a top-view schematic illustration of an exemplary rotational soil penetrometer coupled to a drive system, according to some embodiments.
Figure 11B:
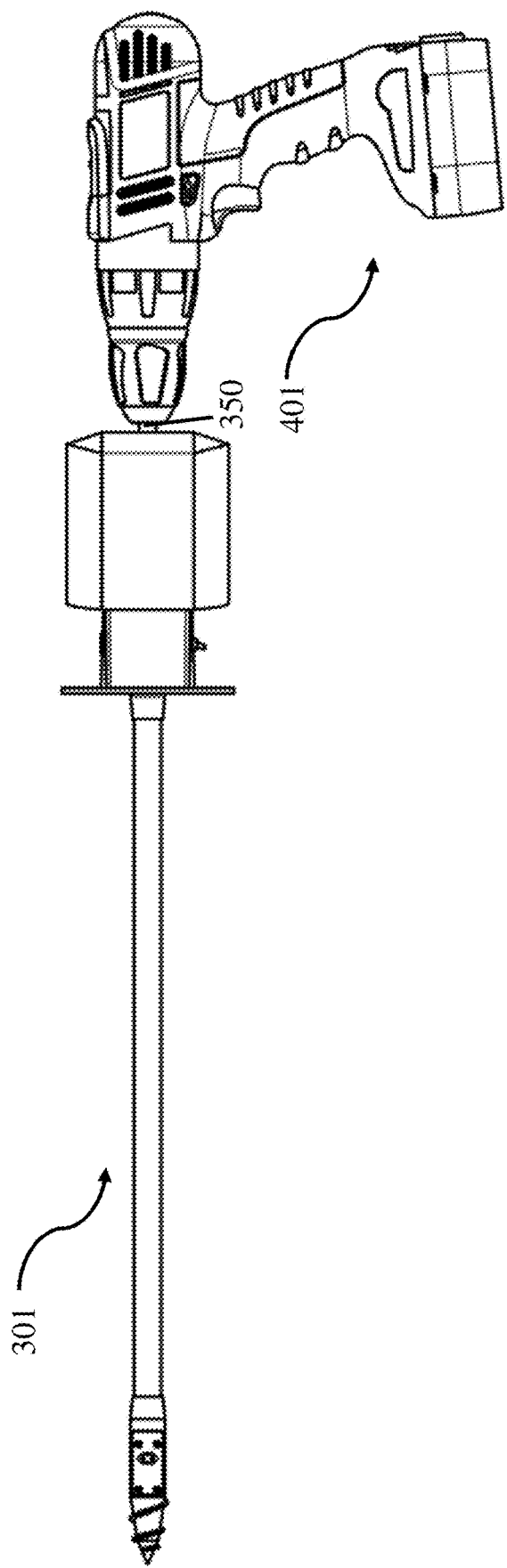
FIG. 11B presents a side-view schematic illustration of an exemplary rotational soil penetrometer coupled to a drive system, according to some embodiments.

In some embodiments, the rotational soil penetrometer is operatively connected to a drive system. For instance, FIGS. 11A-11B present rotational soil penetrometer 301 operatively connected to a drive system 401, according to some embodiments. As one, non-limiting example, the drive system may be a drill. For instance, the drive system may be a hand-drill, as illustrated in FIGS. 11A-11B, though other hand-held or mounted drive motors may be used, as the disclosure is not so limited. Of course, other drive systems are also contemplated, as the disclosure is not so limited. In some embodiments, a proximal end portion of the drive shaft is configured to be selectively received in or otherwise connected to a drill or other drive system, though permeant non-removable connections may also be used. For example, drive system 401 may be operatively coupled to drive shaft 350, as shown in FIGS. 11A-11B, at a proximal end portion 352 of drive shaft 350, shown in FIG. 5. In either case, the rotation speed of the rotational soil penetrometer may be controlled by the drive system. In some embodiments, this design advantageously allows the rotational soil penetrometer to be operated using commonly available, lightweight, and portable drive systems.

According to some embodiments, the rotational soil penetrometer may be rotated at a constant rate during penetration into soil. This may, advantageously, standardize measured values of penetration torque data recorded by the rotational soil penetrometer. In some embodiments, the rotational soil penetrometer is rotated at a particular rate. For example, in some embodiments, the rotational soil penetrometer is rotated at a rate of greater than or equal to 30 RPM, greater than or equal to 40 RPM, greater than or equal to 50 RPM, greater than or equal to 60 RPM, greater than or equal to 70 RPM, or greater. In some embodiments, the rotational soil penetrometer is rotated at a rate of less than or equal to 90 RPM, less than or equal to 85 RPM, less than or equal to 80 RPM, less than or equal to 75 RPM, less than or equal to 70 RPM, less than or equal to 65 RPM, or less. Combinations of these ranges are possible. For example, in some embodiments, the rotational soil penetrometer is rotated at a rate of greater than or equal to 30 RPM and less than or equal to 90 RPM. In some embodiments, the rotational soil penetrometer is configured to be rotated at greater than or equal to 60 RPM and less than or equal to 75 RPM. Of course, ranges both greater than and less than those noted above for both time and distance intervals are also contemplated as the disclosure is not so limited.

The rotational soil penetrometer may be rotated at any of a variety of appropriate speeds when being withdrawn from soil. The rotation rate during withdrawal may be the same as the rotation rate during penetration, or may differ from the rotation rate during penetration. In some embodiments, it is advantageous to withdraw the rotational soil penetrometer at a faster rate than the rate of penetration of the rotational soil penetrometer into the soil. Slow rotation during penetration may be associated with high measurement quality—but if measurements are not recorded during withdrawal of the penetrometer, faster rotation can accelerate the withdrawal process without compromising the integrity of soil measurements. In some embodiments, the rotational soil penetrometer is rotated at a rate of greater than or equal to 30 RPM, greater than or equal to 40 RPM, greater than or equal to 50 RPM, greater than or equal to 60 RPM, greater than or equal to 70 RPM, greater than or equal to 80 RPM, greater than or equal to 90 RPM, greater than or equal to 100 RPM, greater than or equal to 120 RPM, greater than or equal to 140 RPM, greater than or equal to 160 RPM, greater than or equal to 180 RPM, or greater during penetrometer withdrawal. In some embodiments, the rotational soil penetrometer is rotated at a rate of less than or equal to 300 RPM, less than or equal to 280 RPM, less than or equal to 260 RPM, less than or equal to 240 RPM, less than or equal to 220 RPM, less than or equal to 200 RPM, less than or equal to 180 RPM, less than or equal to 160 RPM, less than or equal to 140 RPM, less than or equal to 120 RPM, less than or equal to 100 RPM, less than or equal to 90 RPM, less than or equal to 85 RPM, less than or equal to 80 RPM, less than or equal to 75 RPM, less than or equal to 70 RPM, less than or equal to 65 RPM, or less during penetrometer withdrawal. Combinations of these ranges are possible. For example, in some embodiments, the rotational soil penetrometer is rotated at a rate of greater than or equal to 30 RPM and less than or equal to 300 RPM. Of course, ranges both greater than and less than those noted above for both time and distance intervals are also contemplated as the disclosure is not so limited.

Data may be collected continuously using the rotational soil penetrometer. In some embodiments, continuously collected data may be binned into time and/or distance intervals. For example, continuously collected data may be binned in intervals of greater than or equal to 1 second, greater than or equal to 5 second, greater than or equal to 10 seconds, or greater. In some embodiments, the continuously collected data are binned into time intervals less than or equal to 1 minute, less than or equal to 30 seconds, less than or equal to 15 seconds, or less. Combinations of these ranges are possible (e.g., time intervals of 1 second and 1 minute). Similarly, collected data may be binned into distance intervals including distances that are greater than or equal to 1 cm, 5 cm, 10 cm, and/or any other appropriate distance interval. The distance interval may be also less than or equal to 50 cm, 25 cm, 10 cm, and/or any other appropriate distance interval. Combinations of the foregoing are contemplated including, for example, distance intervals that are between or equal to 1 cm and 50 cm. Of course, ranges both greater than and less than those noted above for both time and distance intervals are also contemplated as the disclosure is not so limited.

In some embodiments, rapid rotation of the soil reduces data quality, by allowing less exposure of the optics module to the soil at a particular depth. In some embodiments, slow rotation of the soil reduces data quality related to measuring penetration torque data, since penetration torque is related to the rate of rotation of the rotational soil penetrometer. Therefore, in some embodiments the range of rotation rates described in the previous paragraph may advantageously permit high quality measurement of mechanical soil data and spectroscopic data. Notably, the preferred rotation rate may depend, in some embodiments, on the type of soil. For example, depending on the soil texture, the preferred rate of rotation for measuring penetration torque may vary, depending on the amplitude of the penetration torque measured from the soil.

The drive system may, in some embodiments, include a handle to improve ease of use. For example, FIGS. 12A-12B show rotational soil penetrometer 301 and drive system 401 as shown in FIGS. 11A-11B, where drive system 401 has been fitted with handle 440. As shown in FIGS. 12A-12B, handle 440 is coupled to drive system 460 via a ring-mount rigidly connected to drive system 401 such that handle 440 does not rotate during operation of drive system 401. Generally speaking, the ring-mount is not necessary, and the handle may be coupled to the drive system by any of a variety of methods known to those of ordinary skill in the art. A handle may be oriented on either side of the drive system, such that a user can operate the drive system with a first hand of their choosing, and grip the handle with their second hand.

Figure 13:
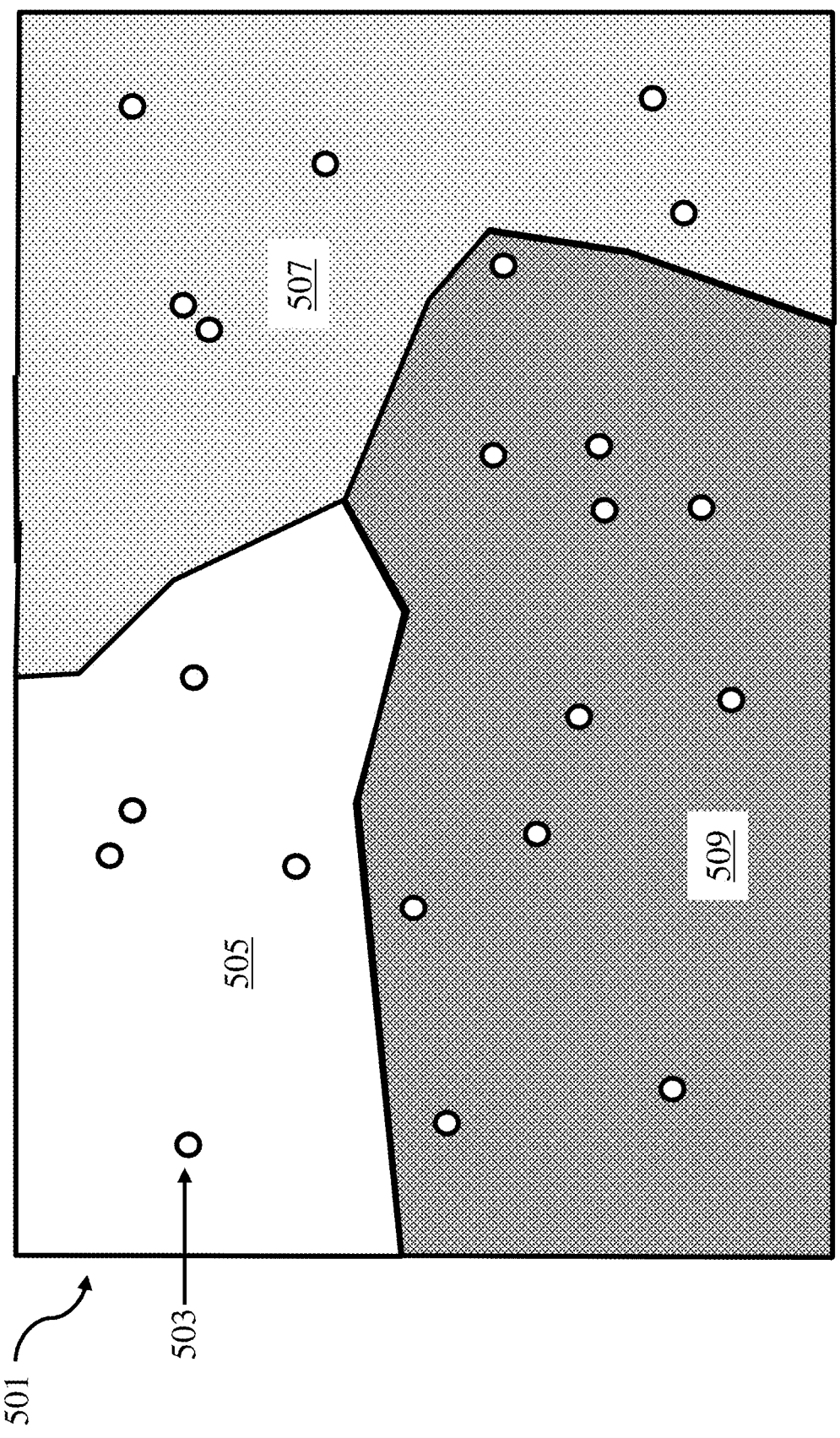
FIG. 13 presents an exemplary schematic illustration of a geographic territory divided into geographic regions associated with different calibrated models, according to some embodiments.

FIG. 13 illustrates an exemplary map of a geographic territory 501, divided into a first geographic region 505, a second geographic region 507, and a third geographic region 509. Depending on the size scale, these regions may either be local field sized regions, or may correspond to large scale geographic regions (e.g., regions of states, countries, and/or continents). For example, a geographic region may have an area of greater than or equal to 1 km$^2$, greater than or equal to 5 km$^2$, greater than or equal to 10 km$^2$, greater than or equal to $1 \times 10^3$ km$^2$, greater than or equal to $1 \times 10^4$ km$^2$, greater than or equal to $1 \times 10^5$ km$^2$, or greater. In some embodiments, the geographic region has an area of less than or equal to $8.5 \times 10^7$ km$^2$, less than or equal to $1 \times 10^7$ km$^2$, less than or equal to $1 \times 10^6$ km$^2$, less than or equal to $1 \times 10^5$ km$^2$, less than or equal to $1 \times 10^4$ km$^2$, less than or equal to $1 \times 10^3$ km$^2$, less than or equal to $1 \times 10^2$ km$^2$, less than or equal to 10 km$^2$, or less. Combinations of these ranges are also possible. For example, in some embodiments, the geographic region has a geographic area of greater than or equal to 1 km$^2$ and less than or equal to $8.5 \times 10^7$ km$^2$.

In some embodiments, bulk soil density within a geographic region of geographic territory 501 may be identified using an appropriate model. The model(s) may be stored on a database, e.g., comprising one or more models associated with one or more geographic region. For example, soil data collected within first geographic region 505 may be analyzed using a first trained statistical model, soil data collected within second geographic region 507 may be analyzed using a second trained statistical model, and/or soil data collected within third geographic region 509 may be analyzed using a third trained statistical model, in some embodiments. The first, second and/or third trained statistical models may be located on the database, which can provide the appropriately calibrated model in response to the geographic location associated with the soil data.

A statistical model described herein may be used to model wet or dry soil. Although the statistical models described herein may be used for or trained using a rotational soil penetrometer, it should be understood that the resulting statistical models and training methods could be associated with other soil measurement methods, and do not necessarily require use of a rotational penetrometer. For example, a method or statistical model described herein could be used to analyze soil using a linear penetrometer, a rotational penetrometer, or any of a variety of other appropriate soil probes, as the disclosure is not so limited.

Figure 14:
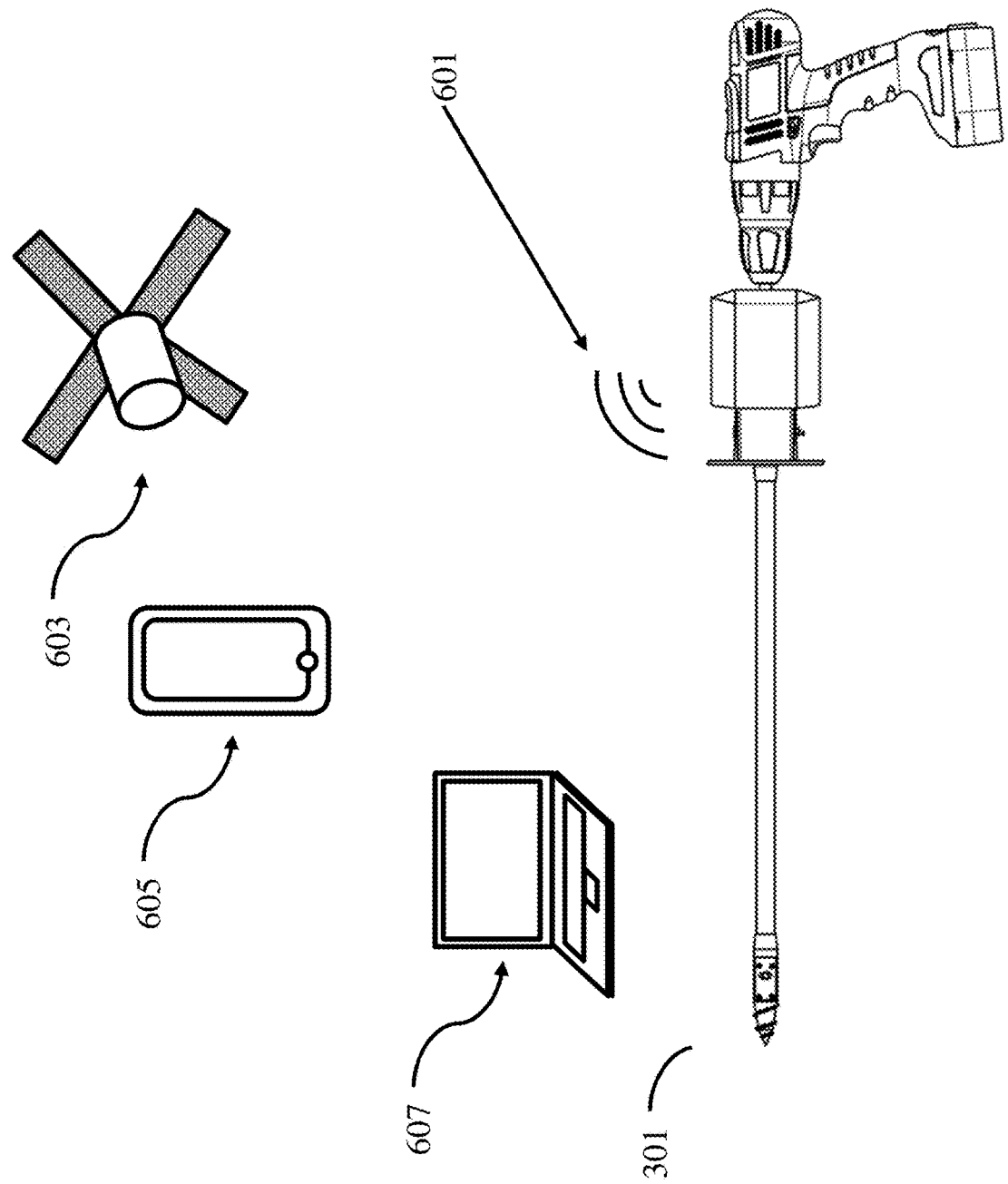
FIG. 14 presents an exemplary schematic illustration of a rotational soil penetrometer transmitting soil and/or location data, according to some embodiments.

The statistical models may be trained using soil data and bulk density measurements collected from a plurality of geographic locations 503 within the geographic territory. Then, an operator of a rotational soil penetrometer within the geographic territory may then transmit soil data from the rotational soil penetrometer to an external database. FIG. 14 schematizes a transmission 601 of soil data and/or location data from rotational soil penetrometer 301 to an external system, such as a database using an intermediate satellite 603, a handheld computing device 605, or computing device 607, which may query and/or update the database with the collected soil data and geographic location in order to identify an appropriate model and determine bulk density of the soil as elaborated on below. Additionally, instances in which the system interacts directly with the database, which may also be referred to as a remotely located computing device in some embodiments, are also contemplated.

Figure 15:
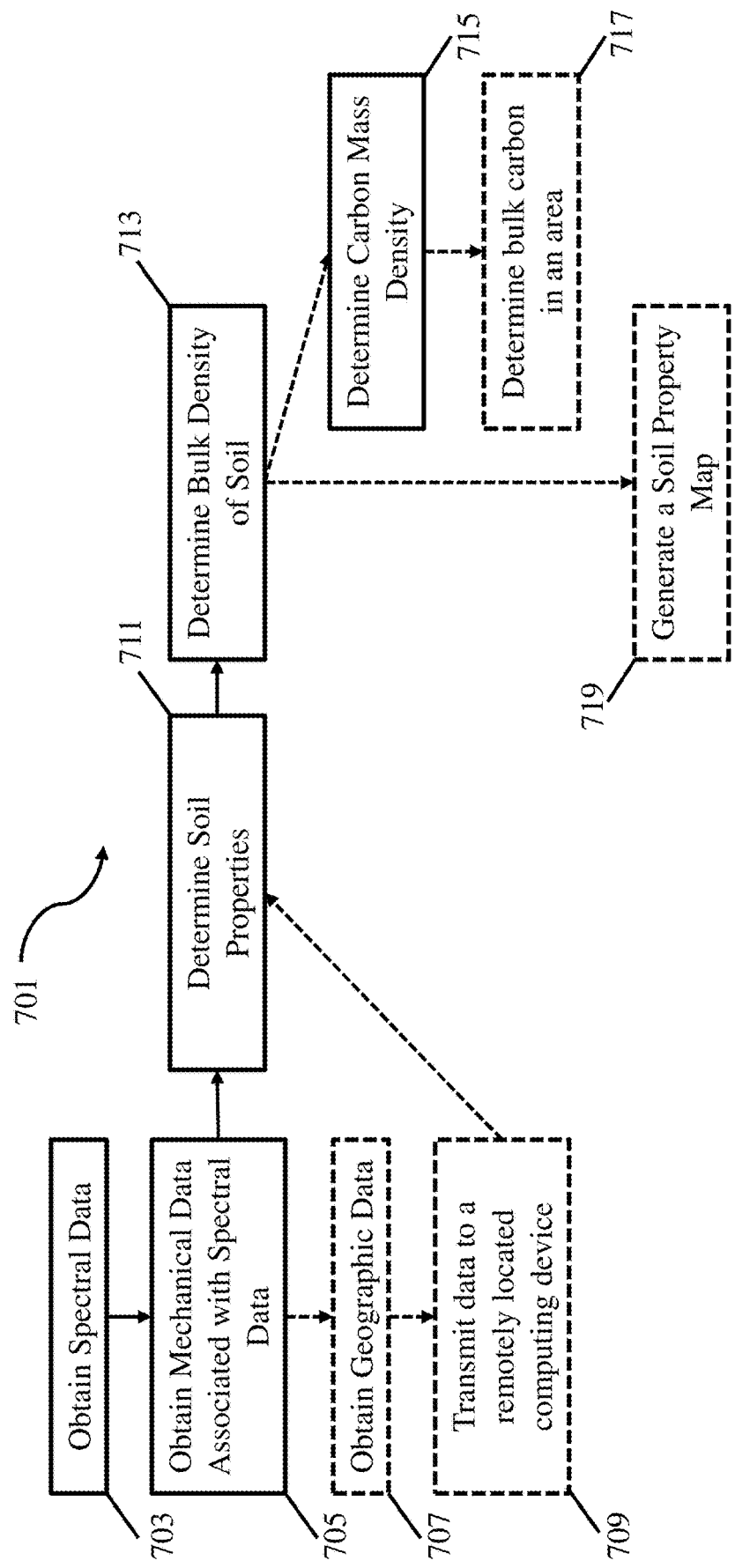
FIG. 15 presents an exemplary schematic illustration of a method of analyzing soil data, according to some embodiments.

FIG. 15 presents a schematic representation of a method 701 of analyzing soil data, according to certain embodiments. In the representation, optional steps are indicated by dashed lines. According to the exemplary method of FIG. 15, first, the rotational soil penetrometer may be used to obtain soil spectroscopic data in step 703, along with mechanical data in step 705 (the mechanical data may comprise, for example, penetration torque data and, optionally, penetration force data). The spectroscopic data may include, for example, NIR and/or mid-IR reflection spectroscopy data that can indicate a density N—H, C—H, and/or O—H bonds, and estimating the soil composition using the results. The mechanical data may be collected simultaneously with the spectroscopic data.

In some embodiments, soil properties (e.g., soil texture, soil moisture, elemental composition) may be optionally determined using the spectroscopic data, as illustrated in step 711. Some properties may be computed simultaneously. For example, it may be advantageous to measure properties such as elemental composition of the soil (e.g., carbon wt. % or nitrogen wt. %), clay content, and/or soil moisture (i.e., water content) simultaneously, by decomposing the reflected intensity. Some properties, such as soil texture, may be determined subsequently, e.g., using an initially determined soil property. For example, in some embodiments the soil texture is determined using clay content and/or moisture content of the soil previously determined. In some embodiments such soil properties may be determined using spectroscopic data alone. These various soil properties may be determined using any appropriately calibrated model.

In some embodiments, the soil data and soil properties are used to determine the bulk density of soil, as illustrated in step 713. The bulk density of the soil may be determined using a model using the soil data and soil properties as inputs. For example, the model may be a trained, statistical model as described above. The model may be configured to take raw soil data (e.g., penetration force data and/or penetration torque data) and one or more soil properties (e.g., soil moisture, soil texture) that are pre-determined from spectroscopic data as inputs to determine the bulk density based on these inputs, as described in greater detail above. Alternatively, in some embodiments, it may not be necessary to determine the soil properties separately. Instead, the raw spectroscopic data and the raw soil data may be input into a model which may then provide the desired bulk density measurement.

According to certain embodiments, it may be advantageous to take optional steps 707, comprising obtaining geographic data, at 709, comprising transmitting the geographic data to a remotely located computing device. For example, the geographic data may be transmitted to a database comprising one or more calibrated models associated with geographic regions and/or used by an associated on board computing device. This may allow the identification of an appropriately calibrated model, which may ultimately improve the accuracy of the bulk density determination of soil in step 713.

Finally, the bulk density may be used to determine the volumetric mass density of carbon, or other elements in the soil, in some embodiments, as represented by step 715 of the method of FIG. 15. As described above, the volumetric mass density of carbon may be determined by determining a wt. % carbon in the soil and multiplying it by the bulk density of the soil. Optionally, the mass of carbon in the topsoil of a given geographic area may be determined in step 717, by multiplying the volumetric mass density of carbon by the volume of the soil in the geographic region. Optionally, by repeating this protocol for a variety of geographic locations, a soil property (e.g., texture, moisture, elemental composition) may be mapped over a given geographic area, as illustrated in step 719. Similar methods may be used for other elements as well.

Figure 16:
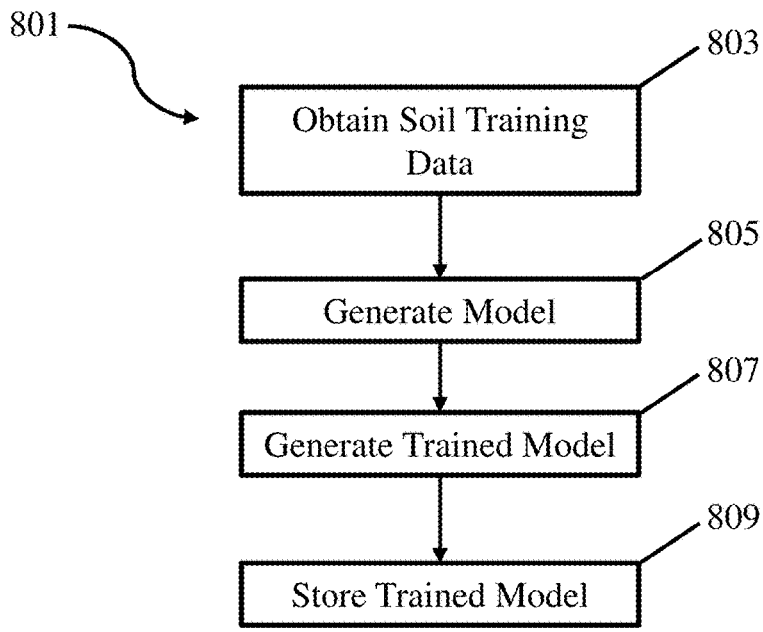
FIG. 16 presents an exemplary schematic illustration of a method of training a statistical model, according to some embodiments.

FIG. 16 represents an exemplary method 801 of training a model for analyzing the bulk density of soil, as described in greater detail above. First, soil training data are provided in step 803, according to some embodiments. The training data may comprise mechanical soil data (e.g., penetration force data and/or penetration torque data) as well as soil properties (e.g., soil moisture and/or soil texture). In some embodiments, the training data originates from a plurality of geographic locations (e.g., counties, states, countries, continents, etc.). In instances where different geographic locations are used, the training data may be sorted into a plurality of associated geographic locations in the separate sets of training data may be used to train separate models associated with a plurality of separate geographic locations as elaborated on further below. In either case, a model (e.g., a machine learning model appropriate to the training data) may be provided in step 805. The training data may be used to train the model, thereby generating a trained model as shown in step 807. The trained model may be appropriate for modeling bulk density of soil associated with the geographic region. Finally, the trained model may be stored in step 809, as described in greater detail above. This may allow the trained model to be recalled in future. For example, the stored model may be used to estimate bulk density associated with soil data collected during a subsequent measurement of soil in the geographic region.

Figure 17:
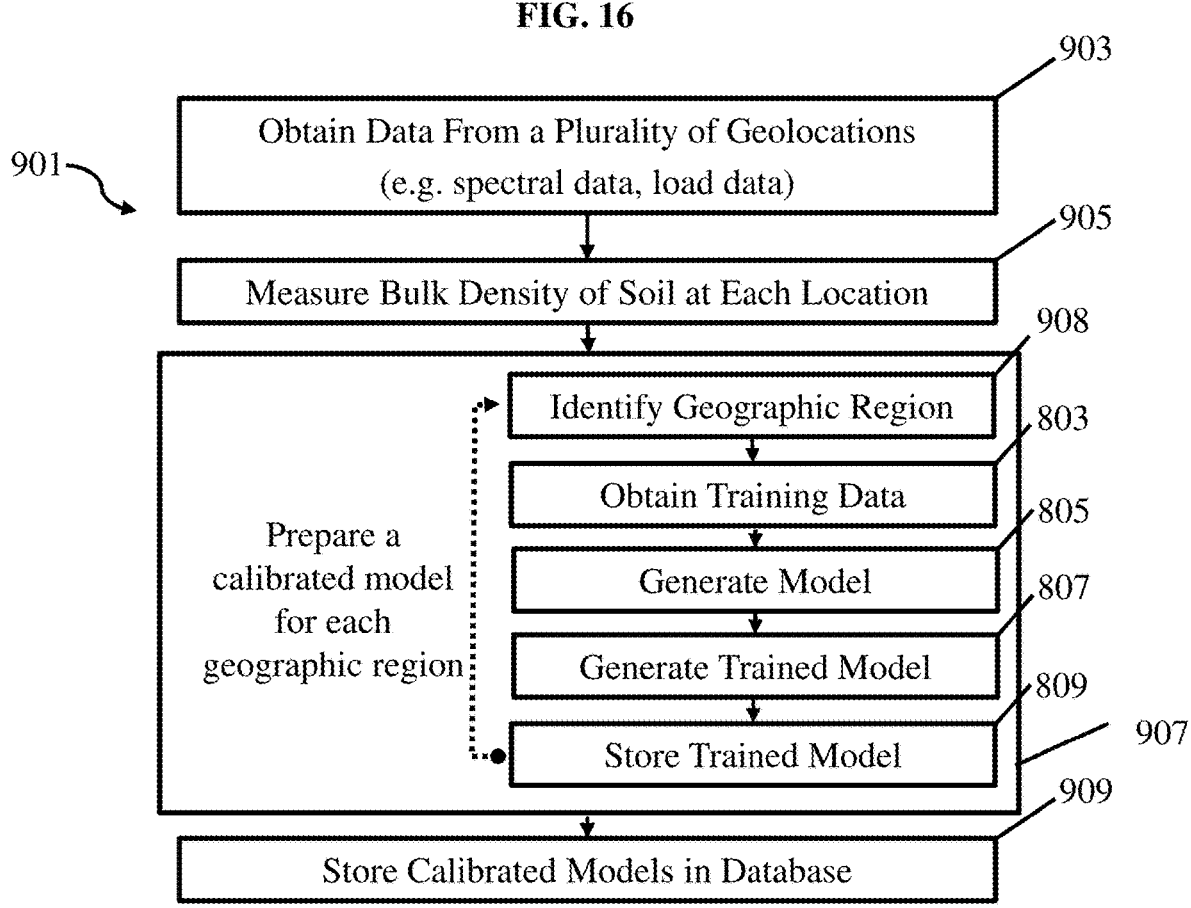
FIG. 17 presents an exemplary schematic illustration of a method of producing a database of calibrated models associated with a plurality of geographic locations, according to some embodiments.

FIG. 17 represents an exemplary method 901 of populating a database of calibrated models associated with a plurality of geographic locations. First, training soil data may be obtained from the plurality of geographic locations, in step 903. Next, the bulk density of the soil associated with the soil data is provided in step 905. Thereafter, calibrated models may be prepared for one or more geographic regions, according to the method of FIG. 16, in step 907. The process of calibrating models for geographic regions is illustrated by the incorporation of step 908 and steps 803, 805, 807, and 809 as part of step 907. In step 908, a particular geographic region is identified. The region may be user determined, or may be determined based on analysis of the data collected from the geolocations. Next, training data associated with the geographic region may be identified based on the geographic locations of the soil data, and the training method described with respect to FIG. 16 can be employed to identify a calibrated model associated with the geographic region. This process may be iterated as necessary to produce calibrated models associated with each geographic region. Finally, the calibrated models may be stored in a database in step 909. Once the database has been provided with calibrated models, it may be accessed to inform analysis of soil data produced by subsequent rotational soil penetrometer measurements.

The above methods may be implemented by at least one processor included in a spectroscope and/or in a system that is separate from a spectroscope used to make the noted measurements. The method may be embodied as computer readable instructions stored on non-transitory computer readable memory associated with the at least one processor such that when executed by the at least one processor the spectroscope and/or system may perform any of the actions related to the methods disclosed herein. Additionally, it should be understood that the disclosed order of the steps is exemplary and that the disclosed steps may be performed in a different order, simultaneously, and/or may include one or more additional intermediate steps not shown as the disclosure is not so limited.

Example: Trained Statistical Model Implementation

This example describes the training and validation of a non-limiting statistical model that may be used to determine a desired soil property. Training data was obtained using a rotational soil penetrometer as described above. The statistical model was a partial least squares regression model and was trained using data from three geographic areas in Illinois and one geographic area in Nebraska. The collected data were smoothed and preprocessed. The training was performed under several testing conditions, and FIGS. 18-20 present non-limiting examples of the training under different test conditions.

Figure 18:
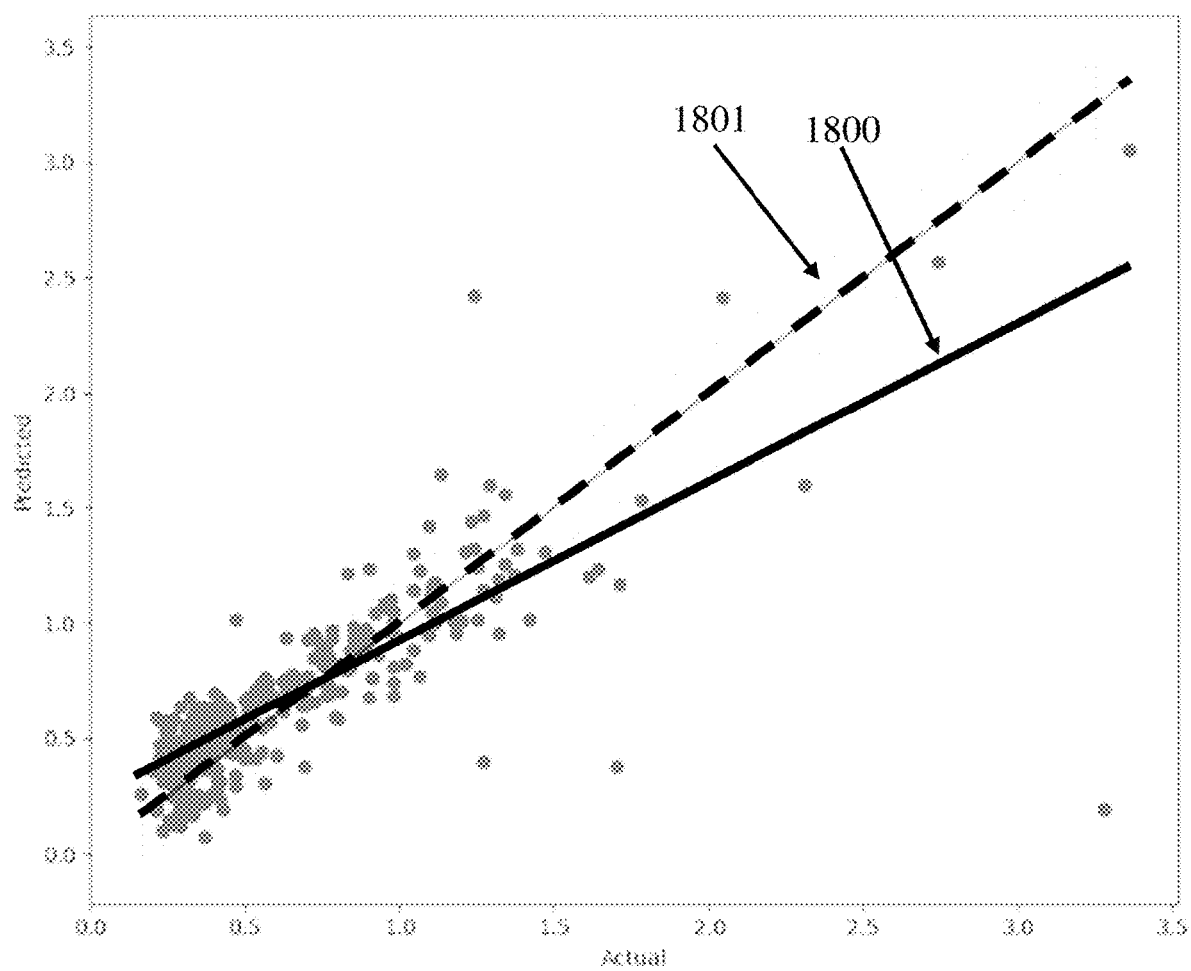
FIG. 18 compares predictions to measured values of carbon content modeled using a non-limiting trained statistical model, according to some embodiments.

FIG. 18 compares actual and predicted values of the soil organic carbon content (SOC) for samples collected from the fields in Illinois. The model was trained using data from two of the fields and validated using data from the third. Trend-line 1800 shows the best fit between measured values for the training data and the predicted values obtained with the trained model. The trendline had a fit with an $R^2$ of 0.63. Dashed line 1801 is the 1:1 line through the origin, representing the limit of perfect accuracy. As shown, trend-line 1800 is relatively close to 1:1 line 1801.

Figure 19:
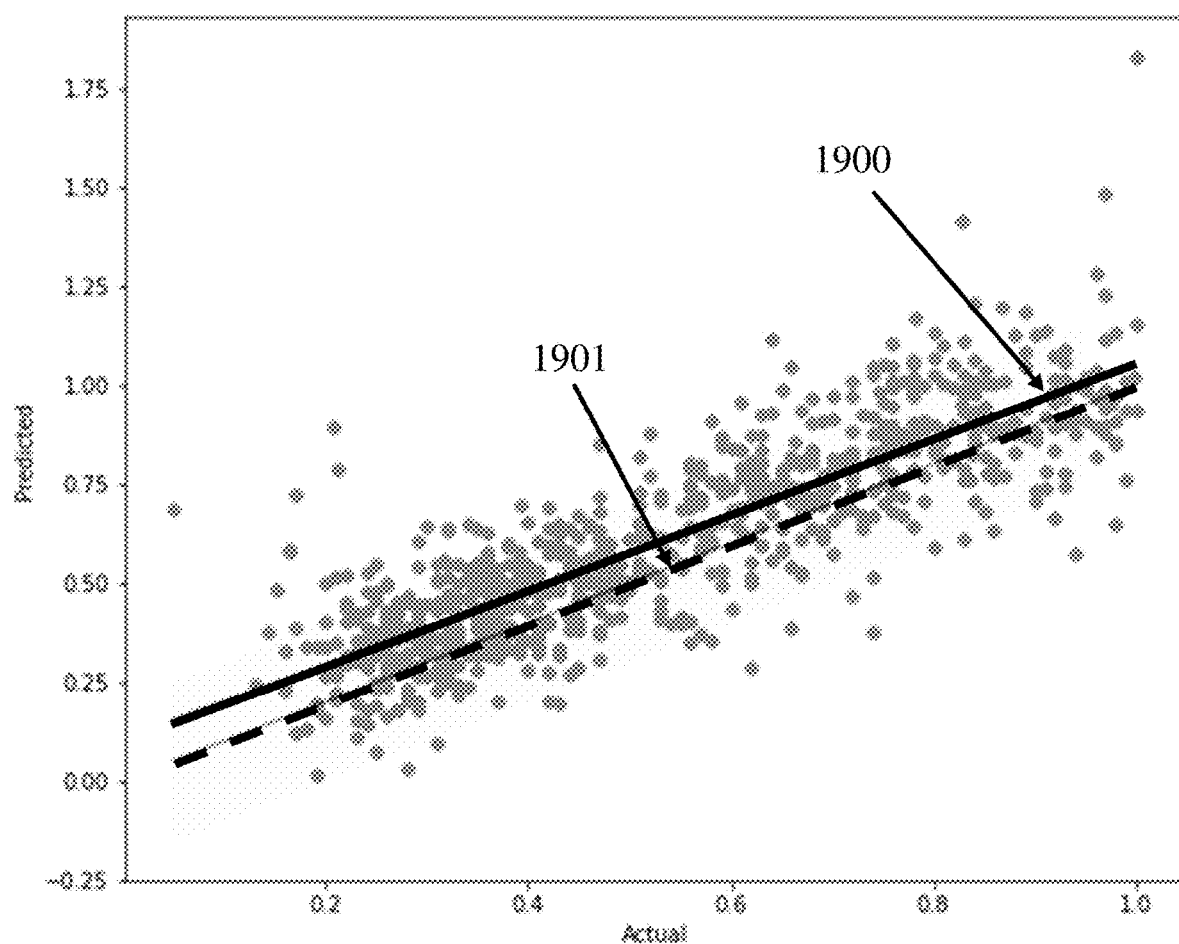
FIG. 19 compares predictions to measured values of carbon content modeled using a non-limiting trained statistical model, according to some embodiments.

FIG. 19 is similar to FIG. 18, but the model was trained using all available data and validated using data with SOC values less than 1. Trend-line 1900 ($R^2=0.71$) again was a good fit to the data and was very similar to 1:1 line 1901.

Figure 20:
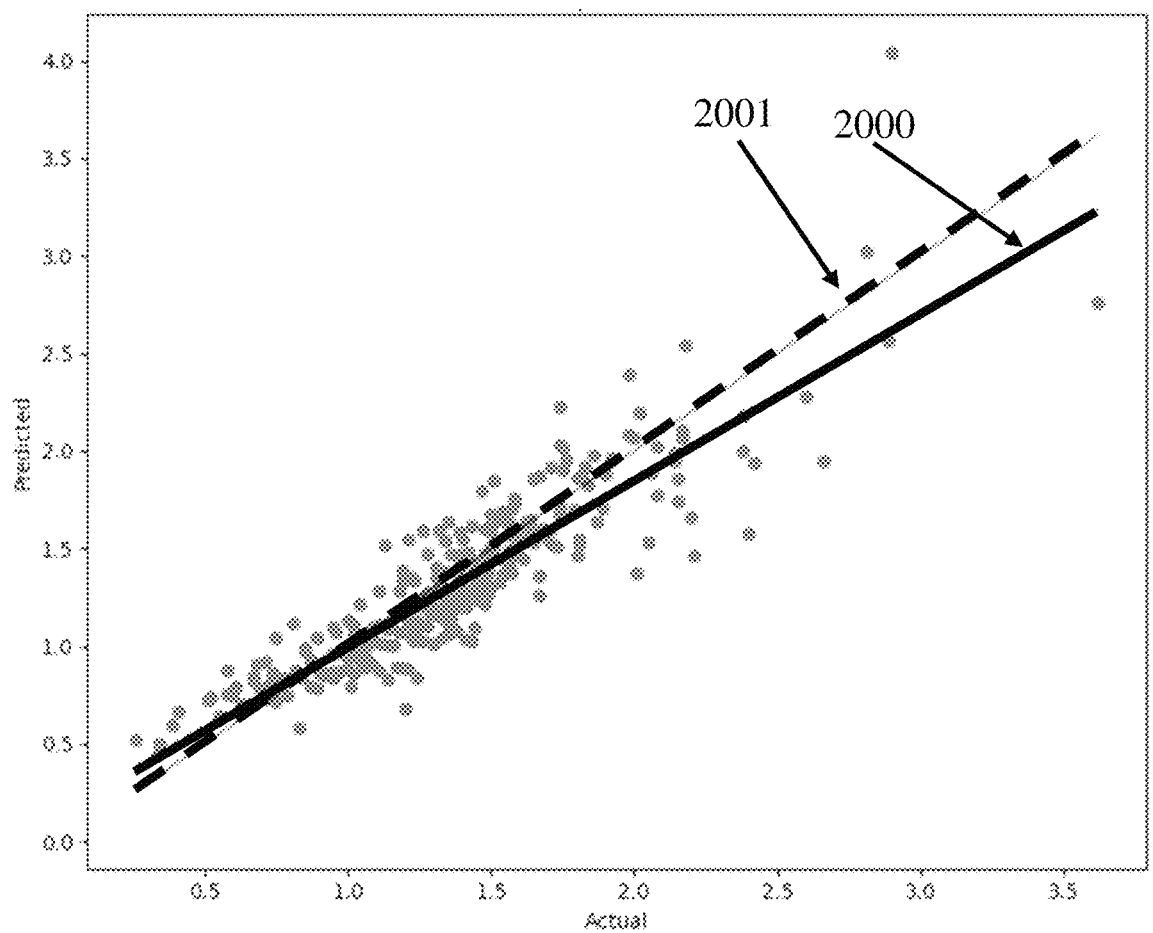
FIG. 20 compares predictions to measured values of carbon content modeled using a non-limiting trained statistical model, according to some embodiments.

FIG. 20 is similar to FIG. 18, but the model was trained using all data from Illinois and 25% of the data from Nebraska, and was validated using the remaining 75% of the data from Nebraska. Trend-line 2000 ($R^2=0.79$) again was a good fit to the data, and was very close to 1:1 line 2001.

Collectively, these results demonstrate the successful training and validation of soil data, and demonstrate that reproducible results could be achieved using this approach. Generally, the trend-line and the 1:1 line fell within the natural variation of the data. Furthermore, these exmaples—in particular, the example of FIG. 18—demonstrate that training on soil from one geographic region can be used to accurately model soil from another geographic region.

The above-described embodiments of the technology described herein can be implemented in any of numerous ways. For example, the embodiments may be implemented using hardware, software or a combination thereof. When implemented in software, the software code can be executed on any suitable processor or collection of processors, whether provided in a single computing device or distributed among multiple computing devices. Such processors may be implemented as integrated circuits, with one or more processors in an integrated circuit component, including commercially available integrated circuit components known in the art by names such as CPU chips, GPU chips, microprocessor, microcontroller, or co-processor. Alternatively, a processor may be implemented in custom circuitry, such as an ASIC, or semicustom circuitry resulting from configuring a programmable logic device. As yet a further alternative, a processor may be a portion of a larger circuit or semiconductor device, whether commercially available, semi-custom or custom. As a specific example, some commercially available microprocessors have multiple cores such that one or a subset of those cores may constitute a processor. Though, a processor may be implemented using circuitry in any suitable format.

Further, it should be appreciated that a computing device may be embodied in any of a number of forms, such as a rack-mounted computer, a desktop computer, a laptop computer, or a tablet computer. Additionally, a computing device may be embedded in a device not generally regarded as a computing device but with suitable processing capabilities, including a Personal Digital Assistant (PDA), a smart phone, tablet, or any other suitable portable or fixed electronic device.

Also, a computing device may have one or more input and output devices. These devices can be used, among other things, to present a user interface. Examples of output devices that can be used to provide a user interface include display screens for visual presentation of output and speakers or other sound generating devices for audible presentation of output. Examples of input devices that can be used for a user interface include keyboards, individual buttons, and pointing devices, such as mice, touch pads, and digitizing tablets. As another example, a computing device may receive input information through speech recognition or in other audible format.

Such computing devices may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the embodiments described herein may be embodied as a computer readable storage medium (or multiple computer readable media) (e.g., a computer memory, one or more floppy discs, compact discs (CD), optical discs, digital video disks (DVD), magnetic tapes, flash memories, RAM, ROM, EEPROM, circuit configurations in Field Programmable Gate Arrays or other semiconductor devices, or other tangible computer storage medium) encoded with one or more programs that, when executed on one or more computers or other processors, perform methods that implement the various embodiments discussed above. As is apparent from the foregoing examples, a computer readable storage medium may retain information for a sufficient time to provide computer-executable instructions in a non-transitory form. Such a computer readable storage medium or media can be transportable, such that the program or programs stored thereon can be loaded onto one or more different computing devices or other processors to implement various aspects of the present disclosure as discussed above. As used herein, the term "computer-readable storage medium" encompasses only a non-transitory computer-readable medium that can be considered to be a manufacture (i.e., article of manufacture) or a machine. Alternatively or additionally, the disclosure may be embodied as a computer readable medium other than a computer-readable storage medium, such as a propagating signal.

The terms "program" or "software" are used herein in a generic sense to refer to any type of computer code or set of computer-executable instructions that can be employed to program a computing device or other processor to implement various aspects of the present disclosure as discussed above. Additionally, it should be appreciated that according to one aspect of this embodiment, one or more computer programs that when executed perform methods of the present disclosure need not reside on a single computing device or processor, but may be distributed in a modular fashion amongst a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

The embodiments described herein may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Further, some actions are described as taken by a "user." It should be appreciated that a "user" need not be a single individual, and that in some embodiments, actions attributable to a "user" may be performed by a team of individuals and/or an individual in combination with computer-assisted tools or other mechanisms.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The invention claimed is:

1. A rotational soil penetrometer, comprising:
   a head comprising a spiral flighting configured to propel the rotational soil penetrometer through soil during rotation of the head;
   a shaft extending from a proximal end portion of the head;
   a bracket, mechanically coupled to a proximal end portion of the shaft;
   and
   a spectrometer mechanically coupled to the shaft and optically coupled to a portion of the head.

2. The rotational soil penetrometer of claim 1, further comprising a torque sensor, configured to measure penetration torque data associated with the rotation of the head into soil, wherein the torque sensor is mechanically coupled to the bracket.

3. The rotational soil penetrometer of claim 1, wherein the head is located at a distal end of the shaft.

4. The rotational soil penetrometer of claim 3, further comprising a force sensor, mechanically coupled to the bracket and configured to measure penetration force data associated with the head located at the distal end of the shaft.

5. The rotational soil penetrometer of claim 1, wherein the spectrometer is optically connected to the head by an optical fiber.

6. The rotational soil penetrometer of claim 1, further comprising a driveshaft operatively coupled to the shaft.

7. The rotational soil penetrometer of claim 6, wherein the driveshaft is operatively coupled to the bracket.

8. The rotational soil penetrometer of claim 1, wherein the head comprises a spiral flighting extending along at least a portion of a length of a distal portion of the head.

9. The rotational soil penetrometer of claim 1, further comprising a cavity formed in the head, wherein the cavity is configured to selectively receive an optics module, wherein the optics module is operatively coupled to the spectrometer through the shaft when the optics module is received in the cavity.

10. The rotational soil penetrometer of claim 1, further comprising the optics module received in the cavity.

11. The rotational soil penetrometer of claim 1, further comprising an optical fiber, extending from the spectrometer to the cavity through the shaft of the rotational soil penetrometer.

12. The rotational soil penetrometer of claim 1, wherein the optics module comprises a window disposed on an exterior surface oriented radially outwards from the head.

13. The rotational soil penetrometer of claim 1, wherein the optics module comprises a light source and one or more optical components configured to direct light from the light source onto soil adjacent to the head and reflected light from the soil to the spectrometer.

14. The rotational soil penetrometer of claim 1, wherein the optics module is configured to measure reflectance from illuminated soil.

15. The rotational soil penetrometer of claim 1, wherein the spectrometer is configured to detect light having a wavelength between 100 nm and 25000 nm.

16. The rotational soil penetrometer of claim 1, wherein the spectrometer is configured to detect light having a wavelength between 750 nm and 5000 nm.

17. The rotational soil penetrometer of claim 1, wherein the rotational soil penetrometer further comprises a force sensor, configured to measure a penetration force data associated with the head.

18. The rotational soil penetrometer of claim 1, wherein the rotational soil penetrometer is configured to determine the moisture, texture, and/or carbon content of the soil spectroscopically.

19. The rotational soil penetrometer of claim 1, wherein the rotational soil penetrometer further comprises a global navigation satellite system (GNSS) receiver.

20. The rotational soil penetrometer of claim 1, wherein a pitch of the flighting increases in a proximal direction along a length of the head.

21. The rotational soil penetrometer of claim 1, further comprising a driveshaft operatively coupled to the shaft.

22. The rotational soil penetrometer of claim 1, coupled to a drive system, optionally wherein the drive system is a hand-drill.

23. The rotational soil penetrometer of claim 1, wherein the optics module comprises a shutter configured to be actuated between an open configuration, wherein the shutter exposes a window of the light module in the open configuration, and wherein the shutter blocks the window of the optics module in the closed configuration.

24. The rotational soil penetrometer of claim 23, wherein the shutter comprises a calibration surface that can provide a reference signal to the spectrometer when the shutter is in the closed configuration.

* * * * *